(12) United States Patent
Reed et al.

(10) Patent No.: US 7,129,269 B2
(45) Date of Patent: Oct. 31, 2006

(54) COMPOUND

(75) Inventors: Michael John Reed, London (GB); Barry Victor Lloyd Potter, Bath (GB)

(73) Assignee: Sterix Ltd., Berkshire (GB)

( * ) Notice: Subject to any disclaimer, the term of this patent is extended or adjusted under 35 U.S.C. 154(b) by 137 days.

(21) Appl. No.: 10/327,500

(22) Filed: Dec. 20, 2002

(65) Prior Publication Data
US 2003/0162752 A1    Aug. 28, 2003

Related U.S. Application Data

(60) Division of application No. 09/638,315, filed on Aug. 14, 2000, now Pat. No. 6,506,792, which is a continuation-in-part of application No. 09/238,345, filed on Jan. 27, 1999, now Pat. No. 6,187,766, which is a division of application No. 09/111,927, filed on Jul. 8, 1998, now Pat. No. 6,011,024, which is a continuation-in-part of application No. PCT/GB97/00600, filed on Mar. 4, 1997.

(30) Foreign Application Priority Data

Mar. 5, 1996   (GB) ................... 9604709.7
Mar. 19, 1996  (GB) ................... 9605725.2

(51) Int. Cl.
*A61K 31/352*   (2006.01)
*C07D 311/74*   (2006.01)

(52) U.S. Cl. ................. 514/456; 514/312; 549/281; 549/403

(58) Field of Classification Search ........... 549/281
See application file for complete search history.

(56) References Cited

U.S. PATENT DOCUMENTS

| | | | |
|---|---|---|---|
| 4,032,545 A * | 6/1977 | Borror | 549/281 |
| 4,600,788 A | 7/1986 | Creuzet et al. | |
| 4,618,622 A | 10/1986 | Schlecker | |
| 4,829,084 A | 5/1989 | Bailey | |
| 4,891,298 A * | 1/1990 | Waller | 430/221 |
| 4,900,727 A | 2/1990 | Kattige et al. | |
| 6,011,024 A | 1/2000 | Reed | |
| 6,187,766 B1 | 2/2001 | Reed | |
| 6,288,107 B1 | 9/2001 | Li | |
| 6,506,792 B1 * | 1/2003 | Reed et al. | 514/456 |

FOREIGN PATENT DOCUMENTS

| | | |
|---|---|---|
| EP | 0 125 195 A1 | 11/1984 |
| EP | 0 241 003 A2 | 10/1987 |
| EP | 0403184 B1 | 8/1990 |
| WO | WO 92/21353 | 12/1992 |
| WO | WO 93/05064 | 3/1993 |
| WO | WO 93/05064 | 4/1993 |
| WO | WO 97/30041 | 8/1997 |

OTHER PUBLICATIONS

L. W. Lawrence Woo, et al., Heteroatom-Substituted Analogues Of The Active-Site Directed Inhibitor Estra-1,3,5(10)-Trien-17-One-3-Sulphamate Inhibit Estrone Sulphatase By A Different Mechanism, J. Steroid Biochem. Molec. Biol. 1996, vol. 57, No. 1/2 p. 79-88.

M. J. Reed et al., The Role Of Cytokines And Sulphatase Inhibitors In Regulating Oestrogen Synthesis In Breast Tumors, J. Steriod Biochem. Molec. Biol., 1995, vol. 53, No. 1-6, p. 413-420.

Atul Purohit, et al., In Vivo Activity of 4-Methylcoumarin-7-O-Sulfamate, A Nonsteroidal, Nonestrogenic Steroid Sulfatase Inhibitor, Cancer Research 56, 1996, p. 4950-4955.

L. W. Lawrence Woo, Active Site Directed Inhibition Of Estrone Sulfatase By Nonsteroidal Coumarin Sulfamates, J. Med. Chem., 1996, 39, p. 1349-1351.

Butenas, et al.; 28606J: 6-Peptidylamino-1-naphthalenesulfonamides Useful as Fluorogenic Proteolytic Enzymes Substrates, Chemical Abstracts 1995; 123(3):28606.

Howarth, et al.; "Estrone Sulfamates: Potent Inhibitors of Estrone Sulfatase with Therapeutics Potential", Journal of Medicinal Chemistry 1994; 37(2):219-221.

Kurano et al.; "290713m: Preparation of Flavone Derivative as Virucides"; Chemical Abstracts 1995; 122(23):1022.

Leonardi, et al.; "225315b: Bicyclic Heterocyclic Derivatives having $\alpha$, -adrenergic and $5HT_{1a}$ Serotonergic Activities", Chemical Abstracts 1997; 126(17):2525316.

Nakai, et al.; "71581U: Preparation of Naphthyloxazolidone Derivatives as Selective Monoamine Oxidase A Inhibitors", Chemical Abstracts 1991, 115(7):796.

(Continued)

*Primary Examiner*—Kamal A. Saeed
(74) *Attorney, Agent, or Firm*—Frommer Lawrence & Haug LLP; Thomas J. Kowalski; Angela M. Collison

(57) ABSTRACT

The instant invention relates to sulphamate compounds of formula I, wherein A represents a ring structure, B represents a ring structure, D a ring structure, C is a bond, E is a link joining ring structure B to the ring structure D, X represents a suitable first group, and Y represents a suitable second group; wherein one ring of the compound is a phenolic ring; and wherein any one of ring structures A, B and D has bound thereto a sulphamate group.

20 Claims, 10 Drawing Sheets

OTHER PUBLICATIONS

Nelson, et al.; "Murine Arylsulfatase C: Evidence for two Isozymes", Experienta 1982; 39:740-742.

Purohit, et al.; "Inactivation of Steroid Sulfatase by an Active Site-Directed Inhibitor, Estrone-3-O-Sulfamate", Biochemistry 1995, 34(36):11508-11514.

Purohit, et al.; "In Vivo Activity of 4-Methylcoumarin-7-O-Sulfamate, A Nonsteroidal, Nonestrogenic Steroid Sulfatase Inhibitor", Cancer Research 1996, 56(21):4950-4955.

Sahm, et al.; "Development of an Oral Formulation for Oestrone 3-O-Sulphate, a Potent Sulphatase Inhibitor", Pharmaceutical Sciences 1996; 2:17-20.

* cited by examiner

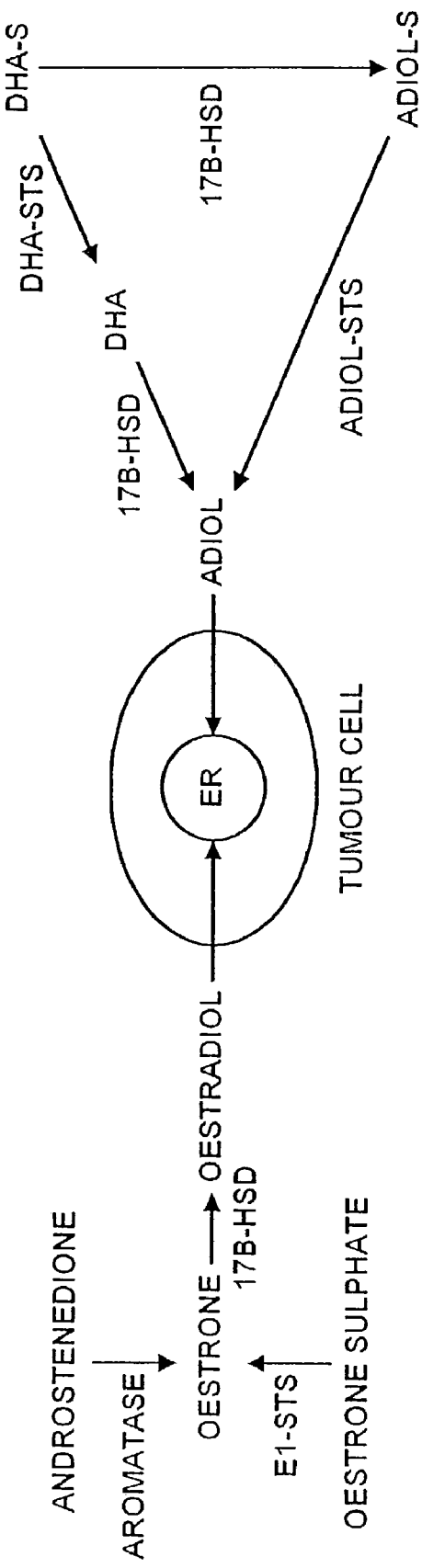

I

II

III

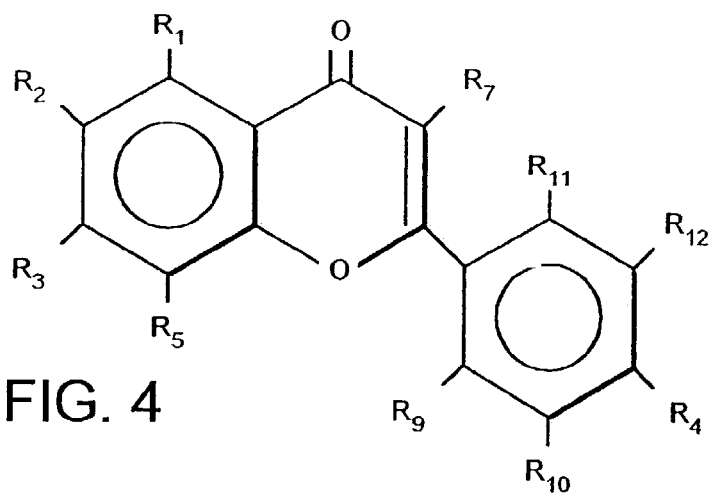
FIG. 4    IV
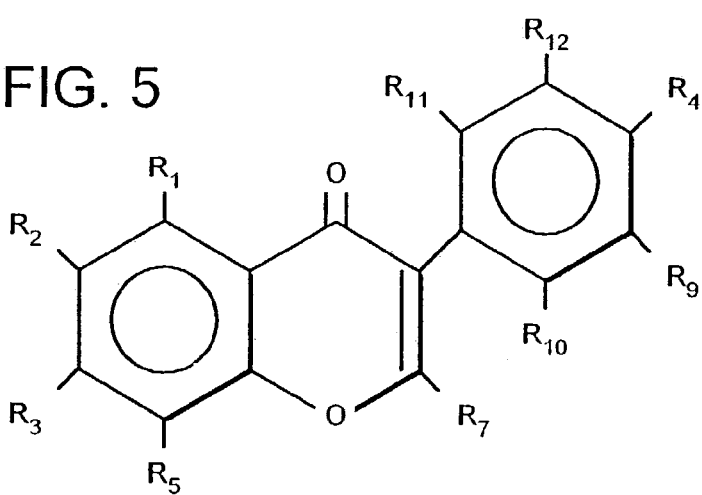
FIG. 5    V
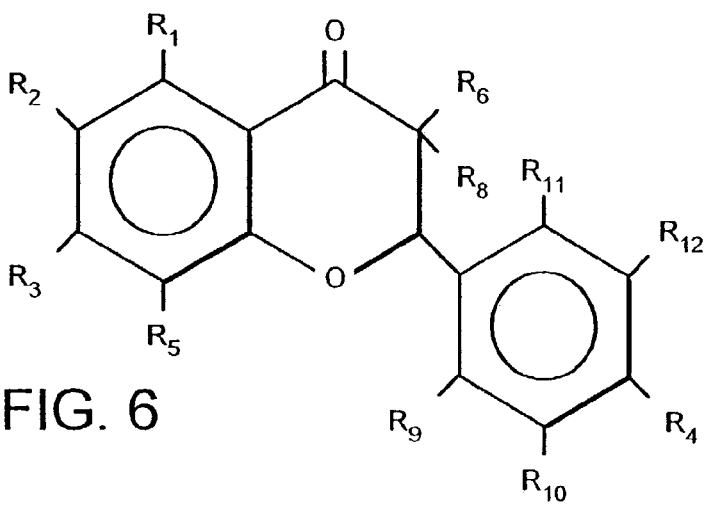
FIG. 6    VI (1a) R= H
(1b) R= SO₂NH₂

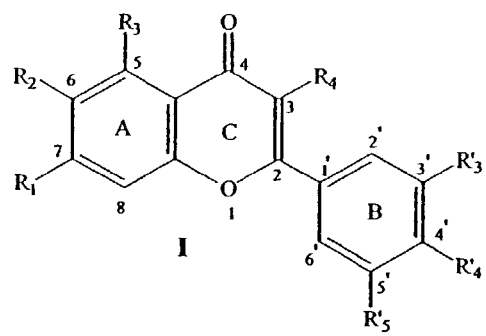

| | R₁ | R₂ | R₃ | R₄ | R'₃ | R'₄ | R'₅ |
|---|---|---|---|---|---|---|---|
| (1) | OSO₂NH₂ | H | H | H | H | H | H |
| (1c) | OH | H | H | H | H | H | H |
| (2) | H | OSO₂NH₂ | H | H | H | H | H |
| (3) | OSO₂NH₂ | H | OH | H | H | H | H |
| (3a) | OCH₃ | H | OH | H | H | H | H |
| (4) | OCH₃ | OSO₂NH₂ | OH | H | H | H | H |
| (5) | OCH₃ | H | OH | H | H | OSO₂NH₂ | H |
| (6) | OCH₃ | OCH₃ | OH | H | OSO₂NH₂ | OCH₃ | H |
| (7) | OCH₃ | OCH₃ | OCH₃ | H | OSO₂NH₂ | OCH₃ | H |
| (8) | H | H | H | H | OSO₂NH₂ | OSO₂NH₂ | H |
| (9) | OSO₂NH₂ | H | OH | H | H | OSO₂NH₂ | H |
| (10) | OSO₂NH₂ | H | OH | OSO₂NH₂ | H | H | H |
| (11) | OSO₂NH₂ | H | OH | OSO₂NH₂ | H | OCH₃ | H |
| (12) | OSO₂NH₂ | H | OH | OSO₂NH₂ | OCH₃ | OCH₃ | OCH₃ |
| (13) | OH | H | OH | OSO₂NH₂ | OCH₃ | OCH₃ | OCH₃ |
| (14) | OSO₂NH₂ | H | H | OSO₂NH₂ | OCH₃ | OCH₃ | OCH₃ |
| (15) | OH | H | H | OSO₂NH₂ | OCH₃ | OCH₃ | OCH₃ |
| (23) | OSO₂CH₃ | H | H | H | H | H | H |
| (24) | OH | OSO₂NH₂ | OH | H | H | H | H |
| (25) | H | H | H | H | H | OSO₂NH₂ | H |
| (26) | H | OSO₂NH₂ | H | H | H | OSO₂NH₂ | H |

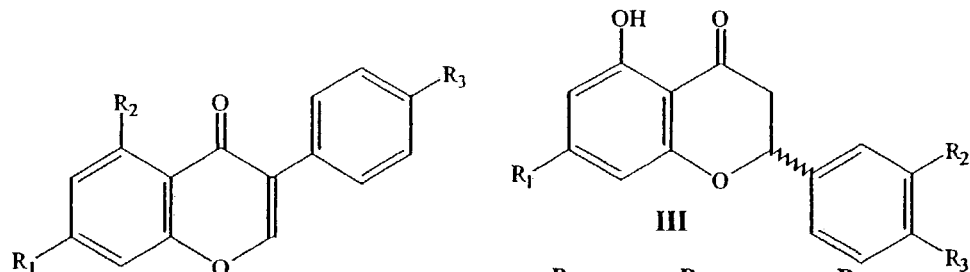

| | R₁ | R₂ | R₃ |
|---|---|---|---|
| (16) | SO₂NH₂ | OH | OCH₃ |
| (17) | SO₂NH₂ | OH | SO₂NH₂ |
| (18) | OH | OH | SO₂NH₂ |
| (19) | SO₂NH₂ | H | SO₂NH₂ |

| | R₁ | R₂ | R₃ |
|---|---|---|---|
| (20) | OH | H | SO₂NH₂ |
| (20a) | OH | H | OH |
| (21) | SO₂NH₂ | SO₂NH₂ | OCH₃ |

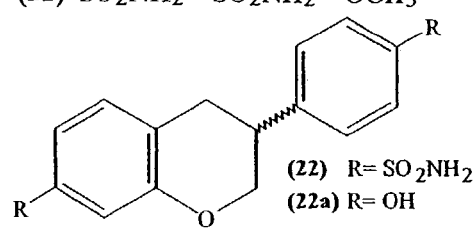

COMPOUND

RELATED APPLICATIONS

This application is a divisional of allowed U.S. application Ser. No. 09/638,315, filed Aug. 14, 2000, now U.S. Pat. No. 6,506,792, as a continuation-in-part of allowed U.S. apllication Ser. No. 09/238,345, filed Jan. 27, 1999, now U.S. Pat. No. 6,187,266 which was a division of U.S. application Ser. No. 09/111,927, filed Jul. 8, 1998, now U.S. Pat. No. 6,011,024, which in turn was a continuation-in-part of inter alia PCT patent application No. PCT/GB97/00600, filed Mar. 4, 1997, designating the U.S. and claiming priority from United Kingdom patent applications 9604709.7 and 9605725.2, filed Mar. 5 and 19, 1996, respectively. PCT/GB97/00600 was published as WO 97/32872 on Sep. 12, 1997. U.S. application Ser. No. 09/142,194, filed Sep. 2, 1998 as the National Phase (35 USC 371) of PCT/GB97/00600 is now U.S. Pat. No. 6,083,978. Each of these applications and patents and each document cited or referenced in each of these applications and patents, including during any prosecution ("application cited documents"), and each document cited or referenced in each of the application cited documents, are hereby incorporated herein by reference. In addition, each document cited in this text ("herein cited documents") and each document cited or referenced in each of the herein cited documents, are hereby incorporated herein by reference.

The present invention relates to a compound.

In particular the present invention relates to a pharmaceutical composition comprising the compound.

Breast and endometrial cancers are major causes of death in Western women. In particular, tumours in endocrine-dependent tissues, such as the breast and endometrium, occur most frequently in postmenopausal women at a time when the ovaries have ceased their production of oestrogens.

Evidence suggests that oestrogens are the major mitogens involved in stimulating and promoting the growth of tumours in endocrine-dependent tissues, such as the breast and endometrium[21]. Although plasma oestrogen concentrations are similar in women with or without breast cancer, breast tumour oestrone and oestradiol levels are significantly higher than in normal breast tissue or blood. In addition, in postmenopausal women oestrogens continue to be produced by extraglandular production in adipose tissue but also in normal and malignant breast tissues[22].

FIGS. 1 and 2 are schematic diagrams showing some of the enzymes involved in the in situ synthesis of oestrone from oestrone sulphate, oestradiol and androstenedione.

In FIG. 2, which schematically shows the origin of oestrogenic steroids in postmenopausal women, "ER" denotes Oestrogen Receptor, "DHA/-S" denotes Dehydroepiandrosterone/-Sulphate, "Adiol" denotes Androstenediol, "E1-STS" denotes Oestrone Sulphatase, "DHA-STS" denotes DHA-sulphatase, "Adiol-STS" denotes Adiol Sulphatase, and "17B-HSD" denotes Oestradiol 17B-hydroxysteroid dehydrogenase.

As can be seen, the main two enzymes that are involved in the peripheral systhesis of oestrogens are the aromatase enzyme and the enzyme oestrone sulphatase.

In short, the aromatase enzyme converts androstenedione, which is secreted in large amounts by the adrenal cortex, to oestrone. Recent reports have suggested that some flavones could inhibit aromatase activity[35,36].

Much of the oestrone so formed, however, is converted to oestrone sulphate (E1S) and there is now a considerable body of evidence showing that E1S in plasma and tissue acts as a reservoir for the formation of oestrone by the action of oestrone sulphatase[23].

In this regard, it is now believed that the oestrone sulphatase (E1-STS) pathway—i.e. the hydrolysis of oestrone sulphate to oestrone (E1S to E1) is the major source of oestrogen in breast tumours[1,2]. This theory is supported by a modest reduction of plasma oestrogen concentration in postmenopausal women with breast cancer treated by aromatase inhibitors, such as aminoglutethimide and 4-hydroxyandrostenedione[3,4] and also by the fact that plasma E1S concentration in these aromatase inhibitor-treated patients remains relatively high. The long half-life of E1S in blood (10–12 h) compared with the unconjugated oestrogens (20 min)[5] and high levels of steroid sulphatase activity in liver and, normal and malignant breast tissues, also lend support to this theory[6].

Thus, oestrogen formation in malignant breast and endometrial tissues via the sulphatase pathway makes a major contribution to the high concentration of oestrogens which are present in these tumours[24,25].

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3- sulphamate and, preferably, oestrone-3-sulphamate (otherwise known as "EMATE").

EMATE is a potent E1-STS inhibitor as it displays more than 99% inhibition of E1-STS activity in intact MCF-7 cells at 0.1 µM. EMATE also inhibits the E1-STS enzyme in a time-dependent and concentration-dependent manner, thereby indicating that it acts as an active site-directed inactivator[7,8].

Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol[8,9]. This is of significance as there is now evidence to suggest that androstenediol may be of even greater importance as a promoter of breast tumour growth[10].

EMATE is also active in vivo as almost complete inhibition of rat liver E1-STS (99%) and DHA-STS (99%) activities resulted when it was administered either orally or subcutaneously[11]. In addition, EMATE has been shown to have a memory enhancing effect in rats[14]. Studies in mice have suggested an association between DHA-STS activity and the regulation of part of the immune response. It is thought that this may also occur in humans[15,16]. The bridging O-atom of the sulphamate moiety in EMATE is believed to be important for inhibitory activity. Thus, when the 3-O-atom is replaced by other heteroatoms—as in oestrone-3-N-sulphamate and oestrone-3-S-sulphamate—these analogues are weaker non-time-dependent inactivators[12].

Thus, EMATE is a potent steroid sulphatase inhibitor which blocks the hydrolysis of both E1S and DHA-S[29-31]. This inhibitor, therefore, not only blocks the synthesis of oestrone from E1S but also the formation of androstenediol from DHA-S.

In addition to oestrone, the other major steroid with oestrogenic properties which is produced by postmenopausal women is androstenediol (see FIG. 2). Androstenediol, although an androgen, can bind to the oestrogen receptor (ER) and can stimulate the growth of ER positive breast cancer cells and the growth of carcinogen-induced mammary tumours in the rat[26,27]. Importantly, in postmenopausal women 90% of the androstenediol produced originates from the androgen dehydroepiandrosterone sulphate (DHA-S) which is secreted in large amounts by the adrenal cortex. DHA-S is converted to DHA by DHA sulphatase, which may be the same as, or different from, the enzyme, oestrone sulphatase, which is responsible for the hydrolysis of E1S[28].

During the last 10–15 years considerable research has also been carried out to develop potent aromatase inhibitors, some of which are currently undergoing clinical evaluation. However, in three recent reports of postmenopausal women with breast cancer who received aromatase inhibitor therapy, plasma E1S concentrations remained between 400–1000 pg/ml[32-34].

In summation therefore in situ synthesis of oestrogen is thought to make an important contribution to the high levels of oestrogens in tumours and therefore specific inhibitors of oestrogen biosynthesis are of potential value for the treatment of endocrine-dependent tumours.

Moreover, even though oestrogen formation in malignant breast and endometrial tissues via the sulphatase pathway makes a major contribution to the high concentration of oestrogens, there are still other enzymatic pathways that contribute to in vivo synthesis of oestrogen.

Thus, there is an urgent need to develop new therapies for the treatment of these cancers.

The present invention therefore seeks to overcome one or more of the problems associated with the prior art methods of treating breast and endometrial cancers.

According to a first aspect of the present invention there is provided a sulphamate compound suitable for use as an inhibitor of both oestrone sulphatase activity and aromatase activity.

In a highly preferred embodiment, the compound of the present invention is a non-steroidal compound.

According to a second aspect of the present invention there is provided a compound having the general formual II wherein F represents a phenolic ring structure (a first ring structure), J represents a third ring structure, I represents a phenolic ring structure (a second ring structure), G is an optional double bond, H is a link joining the second ring structure to the thrid ring structure, and Y represents a suitable second group; wherein any one of ring structures F, J and I has bound thereto a sulphamate group.

According to a third aspect of the present invention there is provided a compound according to the present invention for use as a pharmaceutical.

According to a fourth aspect of the present invention there is provided a compound according to the present invention for inhibiting oestrone sulphatase activity and aromatase activity.

According to a fifth aspect of the present invention there is provided a pharmaceutical composition comprising a compund according to the present invention, and a pharmaceutically acceptable carrier, excipient or diluent.

According to a sixth aspect of the present invention there is provided the use of a compound according to the present invention in the maufacture of a pharmaceutical for inhibiting oestrone sulphatase activity and aromatase activity.

According to a seventh aspect of the present invention there is provided a process for preparing a compound according to the present invention, the process comprising sulphating a flavone, isoflavone or a flavanone.

According to an eighth aspect of the present invention there is provided a process for preparing a compound according to the present invention, the process comprising sulphamaylating a flavone, isoflavone or a flavanone.

In one aspect, therefore, the present invention provides a compound, or a pharmaceutical composition comprising the same, that can affect, such as substantially inhibit, not only the oestrone sulphatase pathway—which pathway converts oestrone to and from oestradiol—but also the aromatase pathway—which pathway converts the androgen precursor androstenedione to oestrone.

This aspect of the present invention is advantageous because by the administration of one type of compound it is possible to block the synthesis of oestrone from both androstenedione and E1S.

In addition, the present invention is further advantageous in that it may also be possible to block the formation of androstenediol from DHA-S.

Hence, the present invention provides compounds that have considerable therapeutic advantages, particularly for treating breast and endometrial cancers.

The compounds of the present invention are different from those disclosed in the prior art because they can act as therapeutic agents that possess both aromatase and steroid sulphatase inhibitory properties.

In a preferred embodiment the compound of the present invention comprises a first ring structure and a sulphamoyl group, which first ring structure may be substituted and/or unsaturated.

Preferably the first ring structure is a phenolic ring structure, which phenolic ring may be substituted.

Preferably, the compound of the present invention further comprises a second ring structure, which second ring structure may be substituted and/or unsaturated.

Preferably the second ring structure is a phenolic ring structure, which phenolic ring may be substituted.

Preferably, the compound of the present invention further comprises a third ring structure which is intermediate the first ring structure and the second ring structure, which third ring structure may be substituted and/or unsaturated.

The present invention will now be described by reference to the Formulae presented in FIGS. 3–9.

In this regard, its is generally preferred that the compound of the present invention has the general formula I wherein A represents the first ring structure, B represents the third ring structure, D represents the second ring structure, C is an optional double bond, E is a link joining the second ring structure to the thrid ring structure, X represents a suitable first group, and Y represents a suitable second group; wherein any one of ring structures A, B and D is a phenolic ring; and wherein any one of ring structures A, B and D has bound thereto a sulphamate group.

Each of the ring structures can independently comprise from 3 and 20 atoms in the ring, preferably from 4 to 8 atoms in the ring. Preferably, ring A and ring D comprise 6 atoms in the ring.

Preferably, the first ring structure and the second ring structure are substituted.

Preferably, any one of ring structures A and D has bound thereto a sulphamate group.

Preferably, each of the first ring and the second ring is a homogeneous ring structure—i.e. the ring is made up of the same atoms.

Preferably, each of the first ring and the second ring comprises only carbon atoms in the ring.

X may be C or C=O. Preferably, X is C=O.

Preferably, the compound of the present invention has the general formula II wherein F represents a phenolic ring structure (the first ring structure), J represents the third ring structure, I represents a phenolic ring structure (the second ring structure), G is an optional double bond, H is a link joining the second ring structure to the third ring structure, and Y represents a suitable second group; wherein any one of ring structures F, J and I has bound thereto a sulphamate group.

Preferably, the third ring structure is a heterogeneous ring structure—i.e. different atoms are in the ring.

Y may be N (including NH, substituted N), C (including $CH_2$, substituted C), O, or S. Preferably, Y is O.

Preferably any one of the ring structures F and I has bound thereto a sulphamate group.

Preferably, link E or link H is a bond.

Preferably, the compound of the present invention is a sulphamate of any one of a flavone, an isoflavone or a flavanone.

Preferably, the compound of the present invention is any one of a compound of the general formula IV, a compound of the general formual V, or a compound of the general formual VI; wherein $R_1$–$R_{12}$ are independently selected from H, OH, a halogen, an amine, an amide, a sulphonamine, a sulphonamide, any other sulphur containing group, a saturated or unsaturated $C_{1-10}$ alkyl, an aryl group, a saturated or unsaturated $C_{1-10}$ ether, a saturated or unsaturated $C_{1-10}$ ester, a phosphorous containing group; and wherein at least one of $R_1$–$R_{12}$ is a sulphamate group.

Preferably, the sulphamate group has the general formula $OSO_2NR_{13}R_{14}$ wherein $R_{13}$ and $R_{14}$ are independently selected from H, OH, a halogen, a saturated or unsaturated $C_{1-10}$ alkyl, an aryl group, a saturated or unsaturated $C_{1-10}$ ether, a saturated or unsaturated $C_{1-10}$ ester.

Preferably, the compound of the present invention is any one of a compound of the general formula IV, a compound of the general formula V, or a compound of the general formula VI; wherein $R_1$–$R_{12}$ are independently selected from H, OH, $OSO_2NR_{13}R_{14}$, O—$CH_3$; wherein at least one of $R_1$–$R_{12}$ is $OSO_2NR_{13}R_{14}$, and wherein $R_{13}$ and $R_{14}$ are defined as above.

Preferably, at least one of $R_{13}$ and $R_{14}$ is H. Preferably, each of $R_{13}$ and $R_{14}$ is H.

Preferably, the compound of the present invention is a sulphamate of any one of the flavone of formula VII, the isoflavone of formula VIII, or the flavanone of formula IX.

Preferably, the compound of the present invention is the sulphamate of any one of formula VII, formula VIII or formula IX.

Preferably, the compound of the present invention is a sulphamate of any one of a flavone, an isoflavone or a flavanone; and wherein the sulphamoyl group is on the C4' atom of the flavone, isoflavone or flavanone. The C4' position has been shown in general Formula III according to the present invention.

Preferably, the compound of the present invention is a flavonoid or flavanoid sulphamate.

In summation the present invention provides compounds that avoid the need for polytherapy. In this regard, the compounds of the present invention can act as therapeutic agents that possess both aromatase and steroid suplhatase inhibitory properties.

Preferably, if the sulphamate group of the compound of the present invention were to be replaced with a sulphate group so as to form a sulphate compound then that sulphate compound would be hydrolysable by an enzyme having steroid sulphatase (E.C. 3.1.6.2) activity.

The compound of the present invention may have one or more sulphamate groups. For example, the compound may be a mono-sulphamate or a bis-sulphamate. For example, in FIGS. 7, 8 and 9 $R_3$ and $R_4$ may be each a sulphamate.

FIGS. 1 and 2 present schematic pathways; FIGS. 3–10 present chemical formulae; and FIG. 11 presents a graph.

BRIEF DESCRIPTION OF THE DRAWINGS

FIGS. 1 and 2 present schematic pathways
FIGS. 3–10 present chemical formulae
FIG. 13 presents a structure of flavonoids

COMPOUNDS SYNTHESISED

Figure 1:
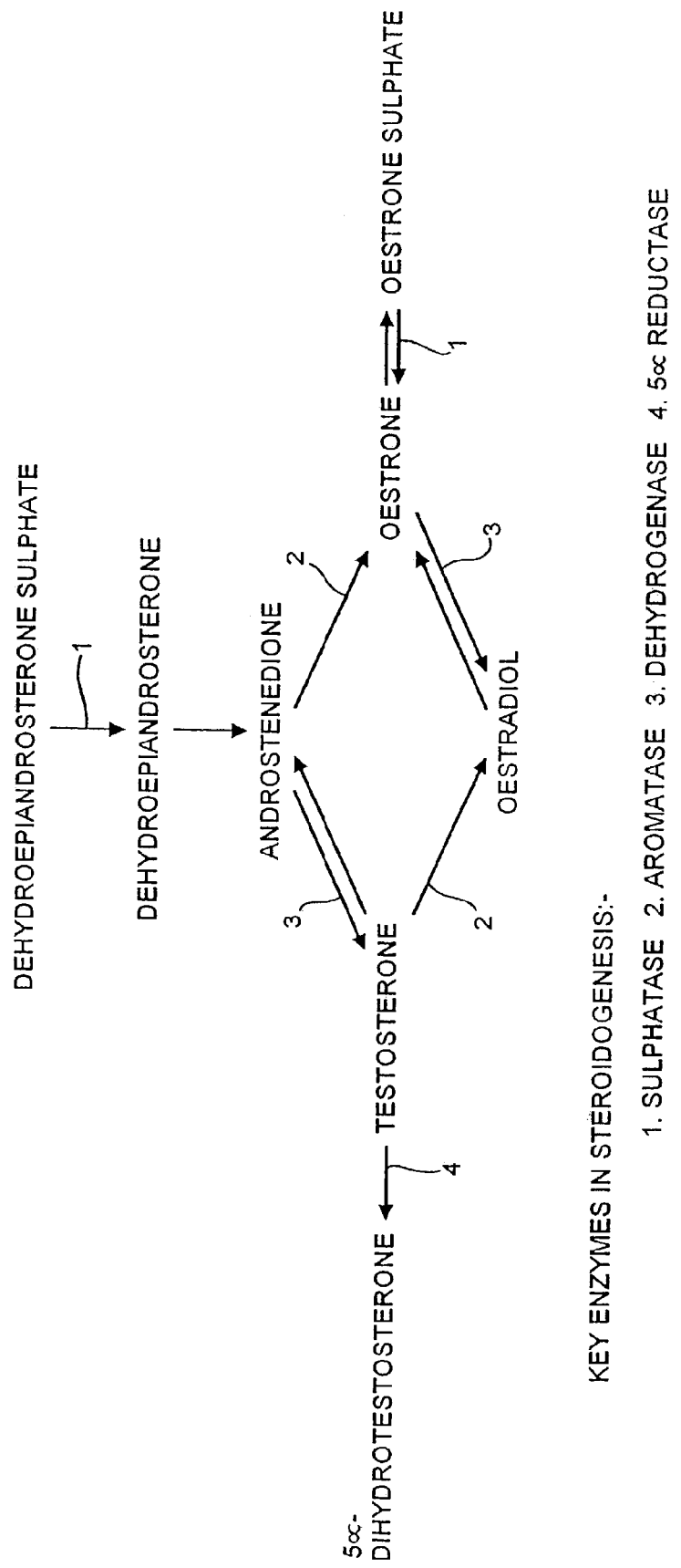
Figure 3A:
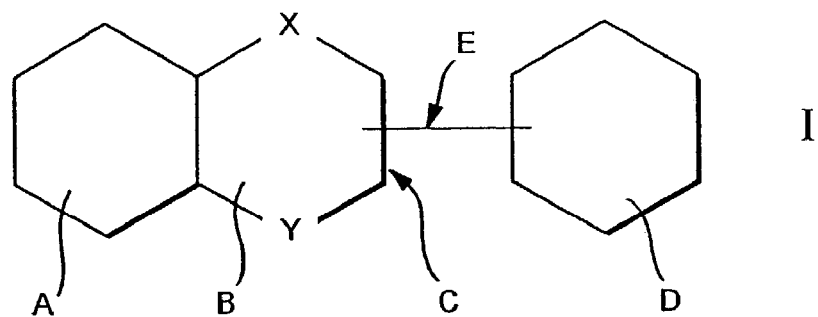
Figure 3B:
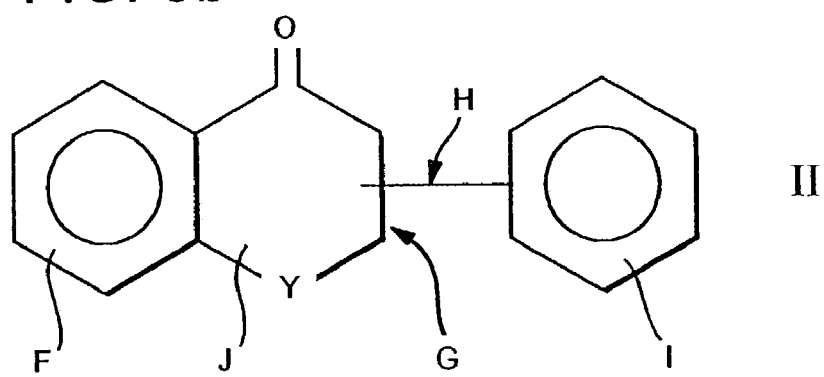
Figure 3C:
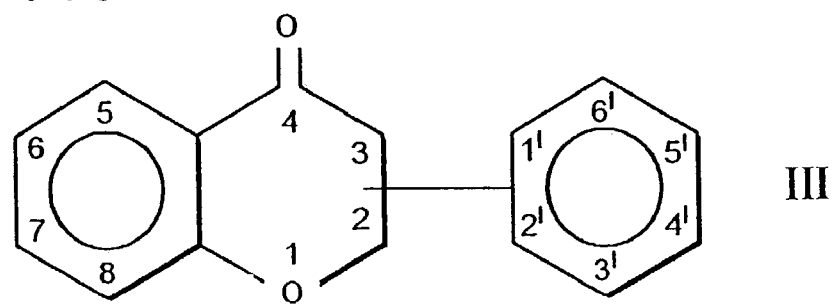
Figure 7:
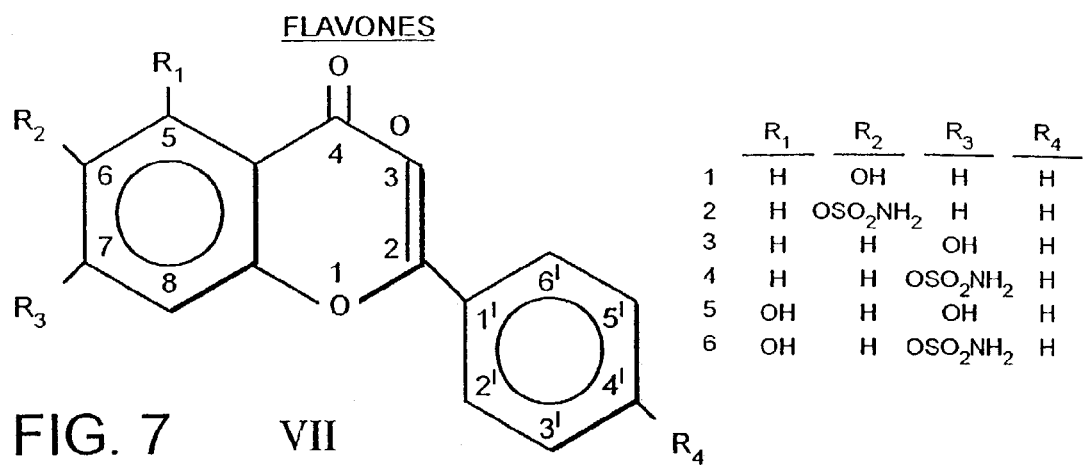
Figure 8:
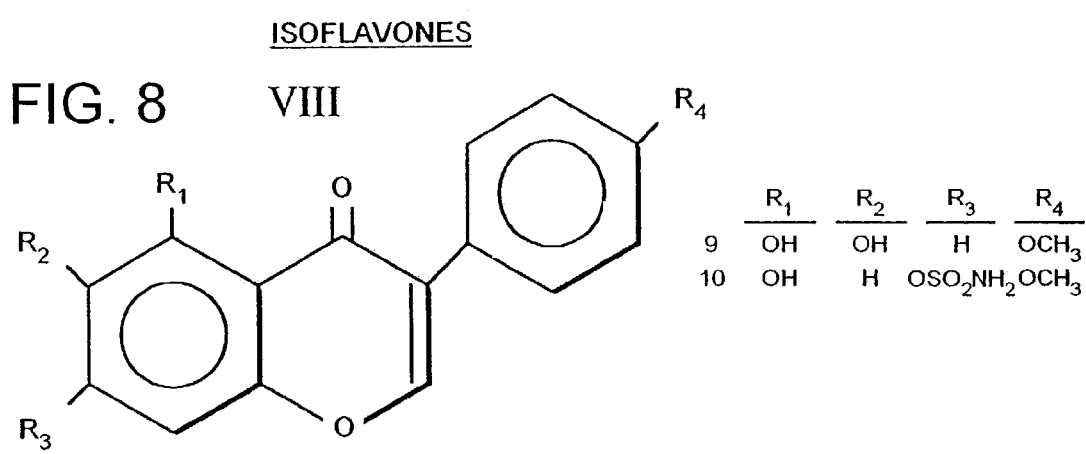
Figure 9:
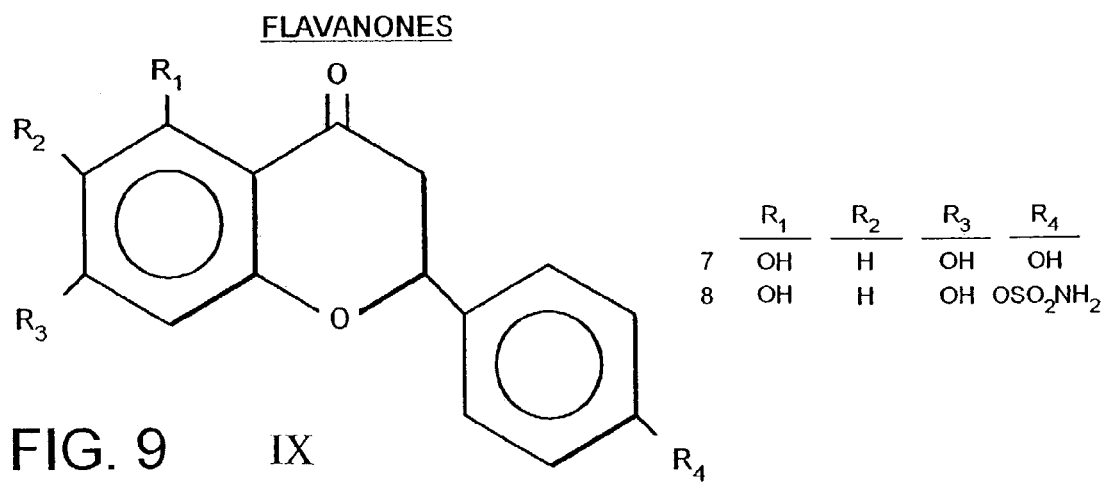
Figure 10:
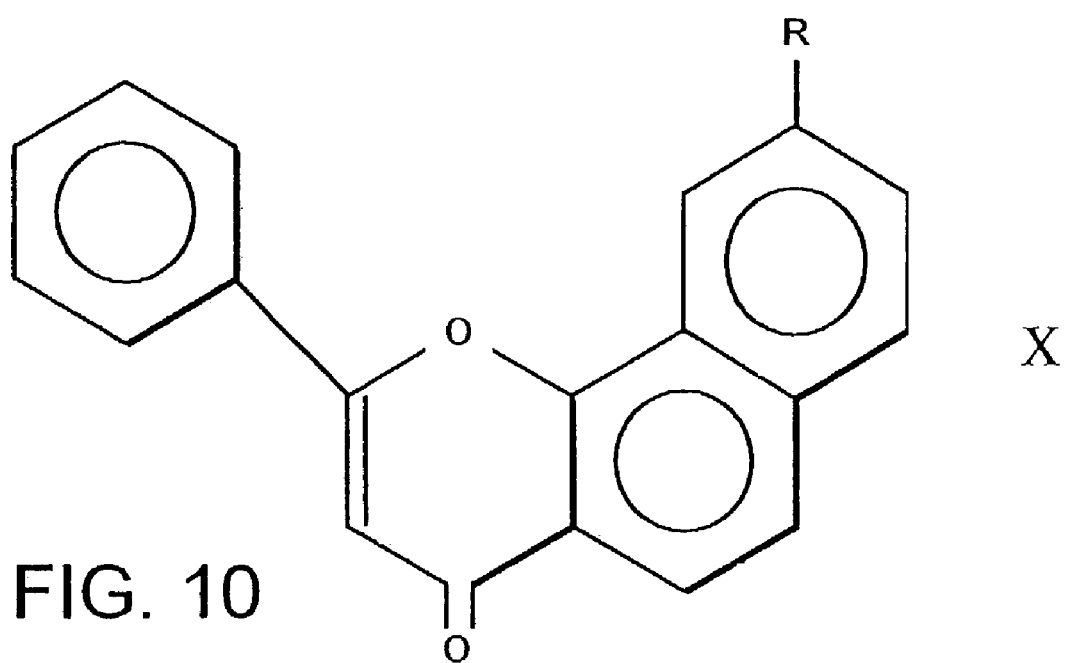

The following sulphamate derivatives were synthesised from the following parent compounds:

| PARENT COMPOUND | SULPHAMATE COMPOUND |
|---|---|
| 1 | 2 |
| 3 | 4 |
| 5 | 6 |
| 7 | 8 |
| 9 | 10 | wherein
1=6-hydroxy flavone
2=flavone-6-sulphamate
3=7-hydroxy flavone
4=flavone-7-sulphamate
5=5,7-dihydroxy flavone
6=5-hydroxy-flavone-7-sulphamate
7=5,7-dihydroxy-4'-hydroxy-flavone
8=5,7-dihydroxy flavanone-4'-flavanone sulphamate
9=5,7-dihydroxy-4'-methoxy-isoflavone
10=5-hydroxy-4'-methoxy-isoflavone-isoflavone-7-sulphamate The formulae are presented in FIGS. 7–9.

SYNTHESIS

The sulphamate derivatives were prepared essentially as described previously[29]. In this regard, a solution of the appropriate flavone, isoflavone or flavanone in anhydrous DMF was treated with sodium hydride (60% dispersion; 1 equiv for 2 and 4; 2 equiv for 6, 8 and 10) at 0° C. under an atmosphere of $N_2$. After evolution of hydrogen has ceased, sulfamoyl chloride (2 equiv except for 8.5 equiv) was added and the reaction mixture was poured into brine after warming to room temperature overnight and diluting with ethyl acetate. The organic fraction was washed exhaustively with brine, dried ($MgSO_4$), filtered and evaporated. The crude product obtained was purified by flash chromatography and recrystallisation to give the corresponding sulfamate.

Flavone 6-O-sulphamate (2)

6-Hydroxyflavone (1.0 g, 4.113 mmol) gave crude product (1.21 g) which was fractionated on silica (200 g) with ethyl acetate. Upon evaporation, the first fraction gave a creamy residue (760 mg, 58.2%) which was recrystallised in warm acetone/hexane (3:2) to give 2 as creamy rod-shaped crystals (557 mg); m.p. 190–191° C.; $R_fs$=0.71 (ethyl acetate), 0.51 (ethyl acetate/hexane, 2:1), vmax (KBr) 3260, 3040, 1620, 1600, 1580, 1370, 1180 cm$^{-1}$; $\delta_H$ (acetone-d$_6$) 6.917 (1H, s, C-3-$\underline{H}$), 7.355 (2H, br s, exchanged with D$_2$O, —OSO—N$\underline{H}$), 7.64 (3H, m, C-3'-$\underline{H}$, C-4'-$\underline{H}$ and C-5'-$\underline{H}$), 7.75 (1H, dd, J$_{C-3-H, C-7-H}$=9 Hz and J$_{C-5-H, C-7-H}$=3 Hz, C-7-$\underline{H}$), 7.87 (1H, d, J$_{C-7-H, C-8-H}$=9 Hz, C-8-$\underline{H}$), 8.02 (1H, d, J$_{C-7-H, C5-H}$=3 Hz, C-5-$\underline{H}$) and 8.13 (2H, m, C-2'-$\underline{H}$ and C-6'-$\underline{H}$). MS: m/z (E.I., rel. intensity) 317.0(11), 304.2(6), 238.0(96), 210.0(16), 187.1(14), 152.0(8), 136.0(100). Acc. MS (E.I): m/z 317.0296, C$_{15}$H$_{11}$NO$_5$S requires 317.0358. Found C, 56.7; H, 3.44; N, 4.31, C$_{15}$H$_{11}$NO$_5$S requires C, 56.78; H, 3.49; N, 4.41%.

Flavone 7-O-sulphamate (4)

7-Hydroxyflavone (700 mg, 2.938 mmol) gave crude product (770 mg) which was fractionated on silica (200 g) with ethyl acetate. Upon evaporation, the first fraction gave a light brown residue (132 mg) which was recrystallised in hot isopropyl alcohol to give 4 as white needle-shaped crystals (60 mg), m.p. 172–174° C. (dec.); R$_f$=0.78 (ethyl acetate), 0.56 (ethyl acetate/hexane, 4.1); vmax (KBr) 3260, 3100, 1630, 1600, 1400, 1580, 1200, 1150 cm$^{-1}$; $\delta_H$ (DMSO-d$_6$/CDCl$_3$, ca. 1:20) 6.824 (1H, s, C-3-$\underline{H}$), 7.396 (1H, dd, J$_{C-5-H, C-6-H}$=8.8 Hz and J$_{C-8-H, C-6-H}$=2.2 Hz, C-6-$\underline{H}$), 7.47 (2H, br s, exchanged with D$_2$O, —OSO$_2$N$\underline{H}_2$), 7.55 (3H, m, C-3'-$\underline{H}$, C-4'-$\underline{H}$ and C-5'-$\underline{H}$), 7.639 (1H, d, J$_{C-6-H, C-8-H}$=2.2 Hz, C-8-$\underline{H}$), 7.92 (2H, m, C-2'-$\underline{H}$ and C-6'-$\underline{H}$) and 8.220 (1H, d, J$_{C-6-H, C-5-H}$=8.8 Hz, C-5-$\underline{H}$). Found: C, 56.5; H, 3.36; N, 4.19, C$_{15}$H$_{11}$NO$_5$S requires C, 56.78; H, 3.49; N, 4.41%.

5-Hydroxyflavone 7-O-Sulphamate (6)

5,7-Dihydroxyflavone (1.0 g, 3.933 mmol) gave crude product (1.13 g) which was fractionated on silica (200 g) with chloroform/acetone (8:1). Upon evaporation, the second fraction gave a yellow residue (324 mg, 24.7%) which was recrystallised in ethyl acetate/hexane (1:1) to give 6 as yellow crystals (213 mg), m.p. 195–200° C. (dec.); R$_f$s=0.21, 0.25 and 0.44 for chloroform/acetone 12:1, 8:1 and 4:1 respectively: vmax (KBr) 3360, 3250, 2925-2850, 1650, 1610, 1380 cm$^{-1}$, $\delta_H$ (acetone-d$_6$) 6.75, 6.98, 7.17 (3H, three s, C-3-$\underline{H}$, C-6-$\underline{H}$, C-8-$\underline{H}$), 7.63 (2H, br s, exchanged with D$_2$O, —OSO-N$\underline{H}_2$), 7.65 (3H, m, C-3'-$\underline{H}$, C-4'-$\underline{H}$ and C-5'-$\underline{H}$), 8.15 (2H, d, J=7.7 Hz, C-2'-$\underline{H}$ and C-6'-$\underline{H}$) and 13.0 (1H, br s, exchanged with D$_2$O, C-5-O$\underline{H}$). MS: m/z (+ve ion FAB in m-NBA, rel. intensity) 440.1(10), 389.3(10), 334.1[100, (M+H)$^+$], 288.1(17), 255.0[25, (M+H−79)$^+$], 169.1(30). MS: m/z (−ve ion FAB in m-NBA, rel. intensity) 499.0(30), 484.1[14, (M−2H+153$^-$], 475.1 (20), 443.1(24), 332.1[100, (M−H)$^-$], 308.1(28), 274.1(20), 253.1[50, (M−H−79)$^-$], 195.1(24). Acc. MS (+ve ion FAB in m-NBA): m/z 334.0392. C$_{15}$H$_{12}$NO$_5$S requires 334.0385. Found: C, 54.0; H, 3.39; N, 4.21. C$_{15}$H$_{11}$NO$_6$S requires C, 54.03; H, 3.33; N, 4.20%.

5,7-Dihydroxyflavanone 4'-O-sulphamate (8)

4',5,7-Trihydroxyflavanone (1.0 g, 3.675 mmol) gave crude product (965 mg) which was fractionated on silica (200 g) with ethyl acetate/hexane (4:1) to give a mixture of the starting flavanone and product. This mixture was further fractionated on silica (200 g) with chloroform/acetone (4:1) and upon evaporation, the second fraction gave a pale yellow oil (345 mg, 34%) which solidified on standing. Subsequent recrystallisation of this solid in ethyl acetate/hexane (1:1) gave 8 as white crystals (259 mg), m.p. 211–213° C.; R$_f$=0.21 (chloroform/acetone, 4:1); vmax (KBr) 3420, 3340, 3260, 3140, 1640, 1510, 1380, 1160 cm$^{-1}$; $\delta_H$ (acetone-d$_6$) 2.84 (1H, dd, J$_{AB}$=17.4 Hz and J$_{ax, eq}$=3.1 Hz, C-3-$\underline{H}_B$), 3.19 (1H, dd, J$_{BA}$=16.9 Hz and J$_{ax,ax}$=12.8 Hz, C-3-$\underline{H}_A$), 5.62 (1H, dd, J$_{ax, eq}$=3.1 Hz, J$_{ax, ax}$=12.8 Hz, C-2-$\underline{H}$), 5.98 (1H, d, J=2.0 Hz, C-6-$\underline{H}$ or C-8-$\underline{H}$), 6.01 (1H, d, J=2.0 Hz, C-6-$\underline{H}$ or C-8-$\underline{H}$), 7.20 (2H, br s, exchanged with D$_2$O, —OSO$_2$N$\underline{H}_2$), 7.40 (2H, d, J=8.7 Hz, C-2'-$\underline{H}$ and C-6'-$\underline{H}$), 7.66 (2H, d, J=8.7 Hz, C-3'-$\underline{H}$ and C-5'-$\underline{H}$), 9.65 (1H, br s, C-7-O$\underline{H}$) and 12.15 (1H, s, C-5-O$\underline{H}$). MS: m/z (+ve ion FAB in m-NBA, rel. intensity) 352.0[100, (M+H)$^+$], 288.1(10), 272.1[14, (M−79)$^-$], 255.2(9), 169.0 (13). MS: m/z (−ve ion FAB in m-NBA, rel. intensity) 701.2(12), 606.2(10), 517.1(42), 504.1[20, (M+153)$^-$], 473.2(10), 350.1[100, (M−H)$^-$], 271.1[45, (M−H−79)$^-$], 182.0(8). Acc. MS (+ve ion FAB in m-NBA): m/z 352.0496, C$_{15}$H$_{14}$NO$_7$S requires 352.0491. Found: C, 51.1; H, 3.68; N, 3.98. C$_{15}$H$_{13}$NO$_7$S requires C, 51.28; H, 3.73; N, 3.99%.

5-Hydroxy-4'-methoxyisoflavone 7'-O-sulphamate (10)

5,7-Dihydroxy-4'-methoxyisoflavone (800 mg, 2.817 mmol) gave crude product (650 mg) which was fractionated on silica (200 g) with chloroform/acetone (8:1). Upon evaporation, the second fraction gave a yellow residue (266 mg, 26%) which was recrystallised in ethyl acetate/hexane (1:1) to give 10 as yellow crystals (211 mg), m.p. 184–188° C.; R$_f$s=0.22 and 0.59 for chloroform/acetone 8:1 and 4:1 resepectively; vmax (KBr) 3300–3020, 1660, 1610, 1400 cm$^{-1}$; $\delta_H$ (acetone-d$_6$) 3.86 (3H, s, —OC$\underline{H}_3$), 6.75 (1H, d, J=2.2 Hz, C-6-$\underline{H}$ and C-8-$\underline{H}$), 7.04 (3H, m, C-6-$\underline{H}$ or C-8-$\underline{H}$ and C-3'-$\underline{H}$ and C-5'-$\underline{H}$), 7.49 (2H, br s, exchanged with D$_2$O, —OSO$_2$N$\underline{H}_2$), 7.58 (2H, d, J=7 Hz, C-2'-$\underline{H}$ and C-6'-$\underline{H}$), 8.41 (1H, s, C-2-$\underline{H}$), 13.05 (1H, br s, exchanged with D$_2$O, C-5-O$\underline{H}$). MS: m/z (+ve ion FAB in m-NBA, rel. intensity) 393.3(12), 364.0[100, (M+H)$^+$], 284.1[12, (M−79)$^+$], 169.1(24), 134.0(22). MS: m/z (−ve ion FAB in m-NBA, rel. intensity) 529.1(25), 515.1[12, (M−H+153)$^-$], 442.1(20), 362.1[100, (M−H)$^-$], 308.1(34), 283.1[70, (M−H−79)$^-$], 170.1(26). Acc. MS (+ve ion FAB in m-NBA): m/z 364.0494, C$_{16}$H$_{14}$NO$_7$S requires 364.0491. Found: C, 52.8; H, 3.65; N, 3.81. C$_{16}$H$_{13}$NO$_7$S requires C, 52.89; H, 3.61; N, 3.85%.

5-Hydroxy Isoflavone-4',7-O,O-Disulphamate (11) and 5,7-Dihydroxy Isoflavone-4'-O-Sulphamate (12)

4',5,7-Trihydroxy isoflavone (0.5 g, 1.85 mmol) upon sulphamoylation gave a crude product (0.65 g) which was fractionated on silica (200 g) with chloroform/acetone (4:1), and upon evaporation the third fraction gave a light yellow residue (0.329 g, 51%) which was recrystallized in ethylacetate/hexane (1:2) to give compound (11) as beige crystals (0.197 g); m.p.=>198° C. (dec); R$_f$s=0.14 and 0.24 for chloroform/acetone 4:1 and 2:1 respectively; v$^{max}$ (KBr) 3460 (—NH$_2$), 1650 (C=O), 1400 (—SO$_2$N—) cm$^{-1}$; $\delta_H$ (acetone-d$_6$) 6.78 (1H, d, J=2.2 Hz, C-6-$\underline{H}$ or C-8-$\underline{H}$, 7.03 (1H, d, J=2.2 Hz, C-8-$\underline{H}$ or C-6-$\underline{H}$), 7.4 (4H, br s, exchanged with D$_2$O, C-4'-OSO$_2$N$\underline{H}_2$ and C-7-OSO$_2$N$\underline{H}_2$), 7.43 (2H, d, J=8.4 Hz, C-3'-$\underline{H}$ and C-5'-$\underline{H}$ or C-2'-$\underline{H}$ and C-6'-$\underline{H}$ and C-6'-$\underline{H}$), 7.72 (2H, d, J=8.4 Hz, C-2'-H and C-6'-H or C-3'-H and C-5'-$\underline{H}$), 8.51 (1H, s, C-2-H) and 12.93 (1H, s, C-5-O$\underline{H}$). MS: m/z (+ve ion FAB in m-NBA, rel. intensity) 428.9[100, (M+H)$^+$], 350.0 [20, (M+H−SO$_2$NH$_2$)$^+$], 272.1 [30, (M−H−SO$_2$NH$_2$)$^+$]. MS: m/z (−ve ion FAB in m-NBA, rel. intensity) 426.9 [100, (M−H)$^-$], 347.9 [95, (M-H-SO$_2$NH$_2$)$^-$], 269.0 [30, (M−H−SO$_2$NH$_2$)$^-$]. Acc. MS: m/z (FAB)$^+$ 429.0083 C$_{15}$H$_{13}$N$_2$O$_9$S$_2$ requires 429.0063. Found C, 42.0; H, 2.91; N, 6.45; C$_{15}$H$_{12}$N$_2$O$_9$S$_2$ requires C, 42.06; H, 2.82; N, 6.54%.

The second fraction was collected and upon evaporation gave light yellow residue (0.112 g, 17%) which was recrystallized in ethylacetate/hexane (1:3) to give compound (12)

as pale white crystals (0.068 g); m.p.=189–192° C. $R_f$s=0.23 and 0.33 for chloroform/acetone 4:1 and 2:1 respectively; $v^{max}$ (KBr) 3500–3300 (—NH$_2$), 3200 (H-bonded-OH), 1680 (C═O), 1610, 1400 (—SO$_2$N—)cm$^{-1}$; $\delta_H$ (acetone-d$_6$) 6.32 (1H, d, J=2.2 Hz, C-6-H or C-8-H), 6.46 (1H, d, J=2.2 Hz, C-8-H or C-6-H), 7.32 (2H, br s, exchanged with D$_2$O,—SO$_2$NH$_2$), 7.42 (2H, t, J=8.4 Hz, C-3'-H and C-5'-H or C-2'-H and C-6'-H), 7.69 (2H, d, J=8.4 Hz, C-2'-H and C-6'-H or C-3'-H and C-5'-H), 8.31 (1H, s, C-2-H), 9.53 (1H, s, C-7-OH) and 12.9 (1H, s, C-5-OH). MS: m/z (+ve ion FAB in m-NBA, rel. intensity) 350.0 [100, (M+H)$^+$], 271.1 [15, (M+H−SO$_2$NH$_2$)$^+$]. MS: m/z (−ve ion FAB in m-NBA, rel. intensity) 347.9 [100, (M−H)$^-$], 269.0 [20, (M−H−SO$_2$NH$_2$)$^-$]. Acc. MS: m/z (FAB)$^+$ 350.0347 C$_{15}$H$_{12}$NO$_7$S requires 350.0335. Found C, 51.0; H, 3.16; N, 3.90; C$_{15}$H$_{11}$NO$_7$S requires C, 51.58; H, 3.17; N, 4.01%.

Isoflavone-4',7-O,O-Disulphamate (13)

4',7-Dihydroxy isoflavone (0.45 g, 1.77 mmol) upon sulphamoylation gave a crude product (0.769 g) which was fractionated on silica (200 g) with chloroform/acetone (4:1), and upon evaporation the second fraction gave a pale white residue (0.553 g, 72%) which was recrystallized in acetone/hexane (1:2) to give the compound (13) as white crystals (0.327 g); m.p.>195° C. (dec.); $R_f$s=0.21 and 0.40 for chloroform/acetone 4:1 and 2:1 respectively; $v^{max}$ (KBr) 3400 (—NH$_2$), 1640 (C═O), 1360 (—SO$_2$N—) cm$^{-1}$. $\delta_H$ (DMSO-d$_6$), 7.37 (2H, d, J=8.8 Hz, C-3'-H and C-5'-H or C-2'-H and C-6'-H), 7.42 (1H, dd, $J_{C-6-H, C-8-H}$=2.2 Hz, $J_{C-6-H, C-5-H}$=8.8 Hz, C-6-H), 7.7 (2H, d, J=8.8 Hz, C-2'-H and C-6'-H or C-3'-H and C-5'-H), 8.09 (2H, br s, exchanged with D$_2$O, —OSO$_2$NH$_2$), 8.24 (1H, d, J=8.8 Hz, C-5-H, 8.36 (2H, br s, exchanged with D$_2$O, —OSO$_2$NH$_2$), 8.63 (1H, s, C-2-H). MS: m/z (+ve ion FAB in m-NBA, rel. intensity) 412.9 [100, (M+H)$^+$], 334.0 [25, (M+H−SO$_2$NH$_2$)$^+$], 255.1 [20, (M+H−SO$_2$NH$_2$)$^+$]. MS: m/z (−ve ion FAB in m-NBA, rel. intensity) 410.9 [100, (M−H)$^-$], 332.0 [70, (M−H−SO$_2$NH$_2$)$^-$], 253.0 [30, (M−H−SO$_2$NH$_2$)$^-$]. Acc. MS: m/z (FAB)$^+$ 413.0119 C$_{15}$H$_{13}$N$_2$O$_8$S$_2$ requires 413.0113. Found C, 44.0; H, 2.94; N, 6.62; C$_{15}$H$_{12}$N$_2$O$_8$S$_2$ requires C, 43.69; H, 2.93; N, 6.79%.

Assay of Inhibition of Sulphatase and Aromatase Activities

Sulphatase inhibition was assessed using placental microsome (100,000 g) preparations or intact MCF-7 breast cancer cells as described previously [29,30]. Placental microsomes were incubated with $^3$H E1S, adjusted to 20 µM with unlabelled substrate, in the absence or presence of inhibitor.

Placental microsomes were also used to assess the aromatase inhibitory properties of the flavanoid sulphamates using a tritiated water release assay[37]. Further placental microsomes (200 µl) were incubated with [1β-$^3$H] androstenedione, 60 nM and 1 mM NADPH in the absence or presence of inhibitor.

Inhibition of Sulphatase and Aromatase Activities

Inhibition of oestrone sulphatase and aromatase activities in placental microsomes by the flavanoid sulphamate derivatives is shown in the Table below.

| COMPOUND | CONCENTRATION µM | % INHIBITION Sulphatase | % INHIBITION Aromatase |
|---|---|---|---|
| Flavone-6-sulphamate | 1 | 26.8 | 1 |
|  | 10 | 89.5 | 6.5 |
| Flavone-7-sulphamate | 1 | — | 55 |
|  | 10 | — | 86 |
|  | 50 | 56.3 |  |
|  | 100 | 75.3 |  |

-continued

| COMPOUND | CONCENTRATION µM | % INHIBITION Sulphatase | % INHIBITION Aromatase |
|---|---|---|---|
| 5-hydroxy flavone-7-sulphamate | 1 | 8 | 5 |
|  | 10 | 21 | 76 |
| 5,7-dihydroxy flavanone 4'-sulphamate | 0.1 | 30.4 | Not tested |
|  | 1 | 79.1 | Not tested |
|  | 10 | 98.1 | Not tested |
| 5-hydroxy-4'-methoxy-isoflavone-7-sulphamate | 1 | 1 | 2 |
|  | 10 | 50.6 | 5 |

From the results, it can be seen that potent inhibition of sulphatase and aromatase activities was detected. For sulphatase inhibition this ranged from 21% at 10 µM by 5-hydroxy flavone-7-sulphamate, to 98% by 5,7-dehydroxy flavanone-4'-sulphamate at 10 µM. Potent aromatase inhibition was also achieved ranging from 6.5% by flavone-6-sulphamate at 10 µM to 86% by flavone-7-sulphamate at 10 µM.

Further In Vitro Testing

The following Table presents in vitro data for three isoflavones that were tested.

| | | IN VITRO ACTIVITY | |
|---|---|---|---|
| | | % Inhibition | |
| Compound | Concentration (µM) | MCF-7 Cells | Placental Microsomes |
| Isoflavone 5-hydroxy-4',7-bissulphamate | 0.1 | 28 | nd |
|  | 1.0 | 90 | nd |
|  | 10.0 | 99 | 93 |
| Isoflavone 5,7-dihydroxy-4'-sulphamate | 0.1 | 23 | nd |
|  | 1.0 | 83 | nd |
|  | 10.0 | 99 | 75 |
| Isoflavone-4',7-bissulphamate | 0.1 | 89 | nd |
|  | 1.0 | 99 | nd |
|  | 10.0 | 99 | 99 | nd = not done

In Vivo Testing

Figure 11:
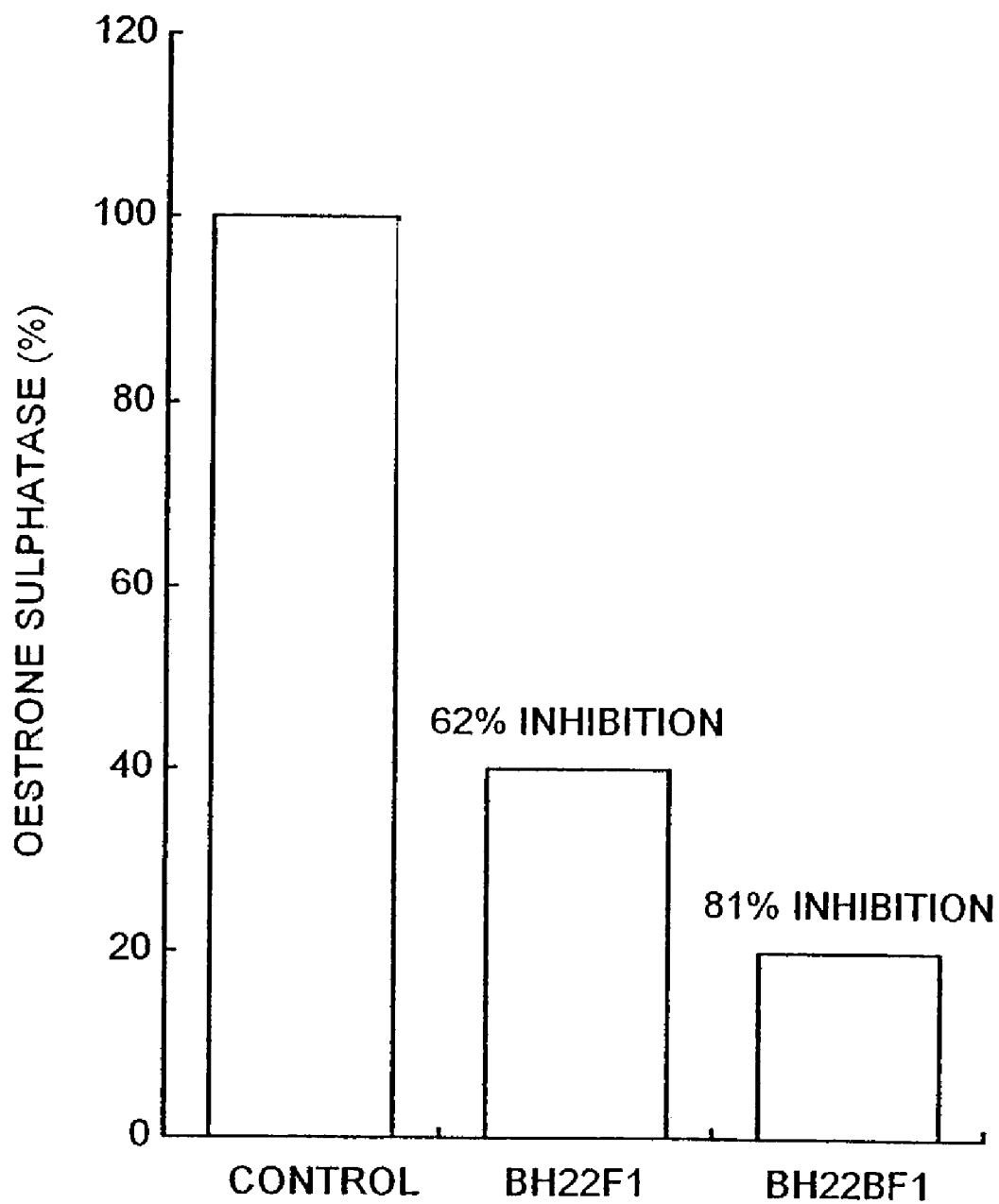
FIG. 11 presents a graph

FIG. 11 presents in vivo inhibition of oestrone sulphatase activity in rat liver for two isoflavones according to the present invention. In this regard, BH22F1=5- hydroxy isoflavone-4',7-bissulphamate; BH22BF1=5,7-dihydroxy isoflavone-4'-sulphamate. Compounds were administered as a single 10 mg/Kg dose. Oestrone sulphatase activity was assayed in tissue samples obtained 24 h after drug administration.

Compounds 14–16

Starting with the appropriate parent compound, the ring system sulphamates according to the present invention were prepared essentially as follows. In this regard, a solution of the appropriate parent compound in anhydrous DMF was treated with sodium hydride [60% dispersion; 1.2 equiv.] at 0° C. under an atmosphere of N$_2$. After evolution of hydrogen had ceased, sulfamoyl chloride in toluene [excess, ca. 5 equiv.] was added and the reaction mixture was poured into brine after warming to room temperature overnight and diluting with ethyl acetate. The organic fraction was washed exhaustively with brine, dried (MgSO$_4$), filtered and evaporated. The crude product obtained was purified by flash chromatography and recrystallisation to give the corresponding sulfamate. All the compounds were fully characterized by spectroscopic and combustion analysis.

Example compounds are as follows:

The following compounds of the present invention are made and are found to be steroid sulphatase inhibitors in accordance with the present invention.

Compounds 14a–14y

Compound 14a

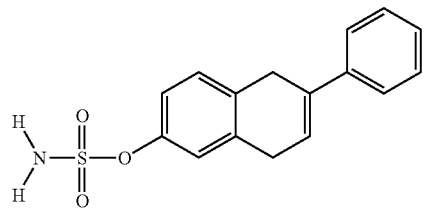

Compound 14b

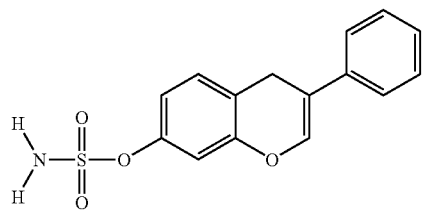

Compound 14c

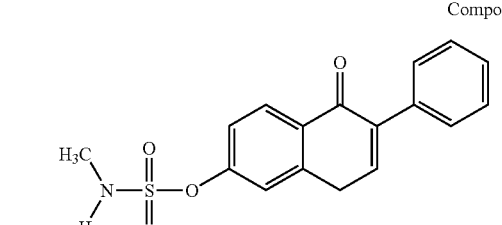

Compound 14d

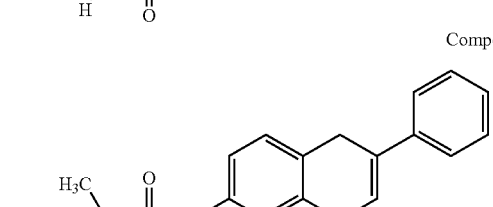

Compound 14e

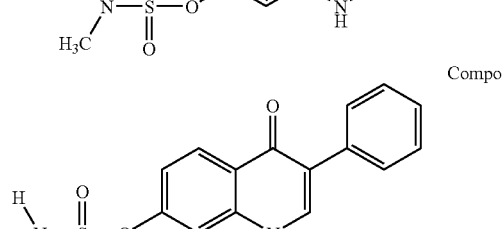

Compound 14f

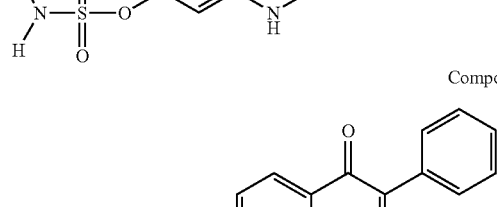

-continued

Compound 14g

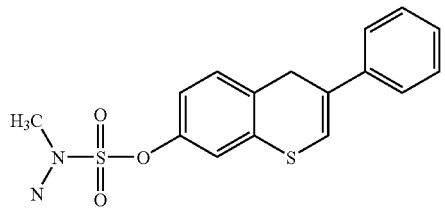

Compound 14h

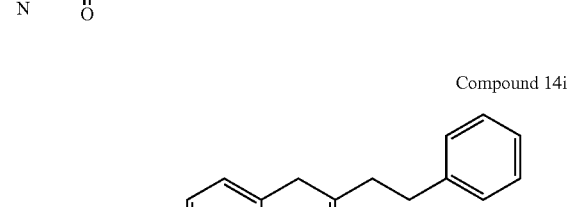

Compound 14i

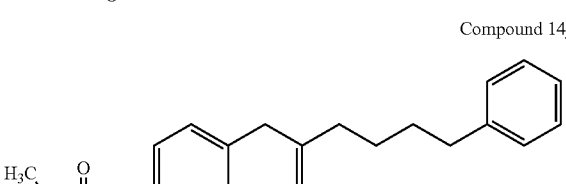

Compound 14j

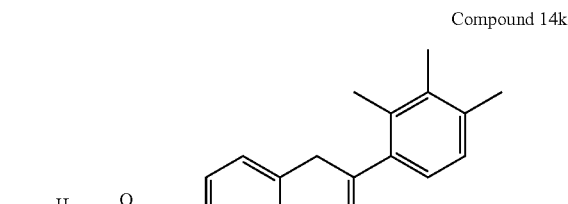

Compound 14k

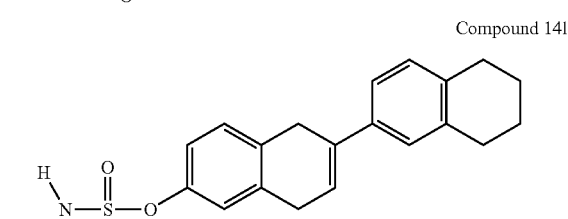

Compound 14l

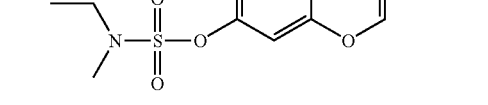

-continued
Compound 14m
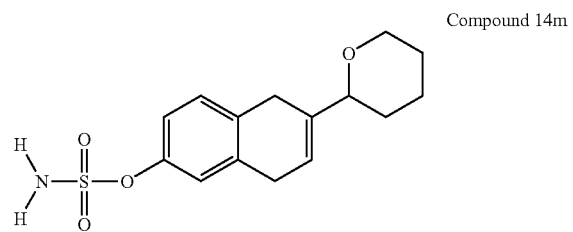
Compound 14n
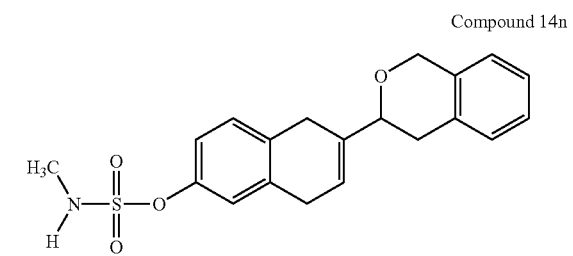
Compound 14o
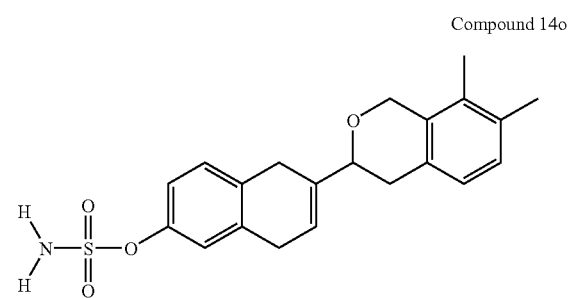
Compound 14p
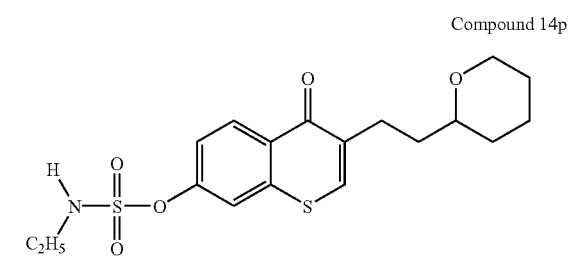
Compound 14q
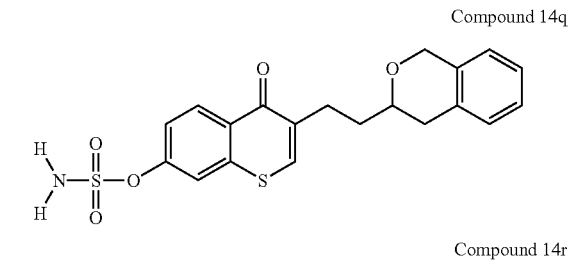
Compound 14r
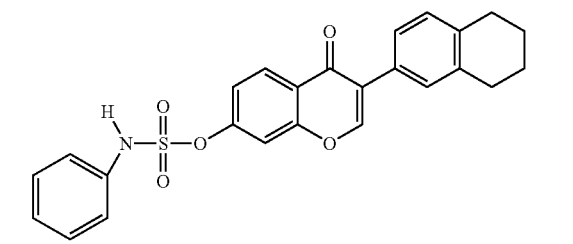
-continued
Compound 14s
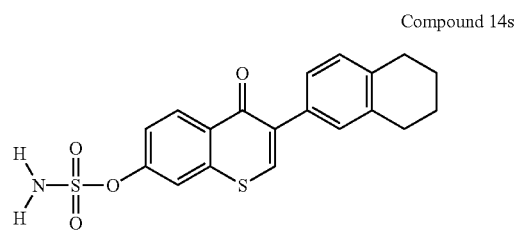
Compound 14t
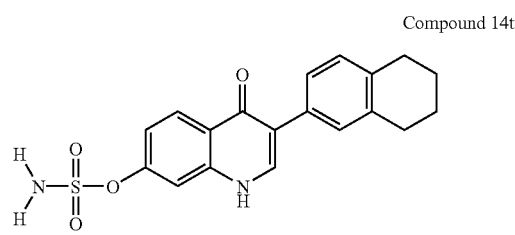
Compound 14u
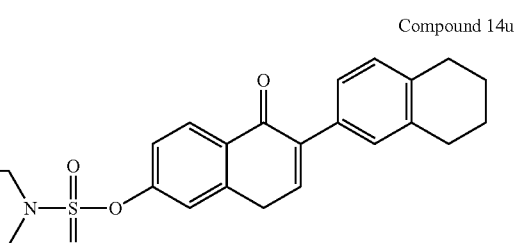
Compound 14v
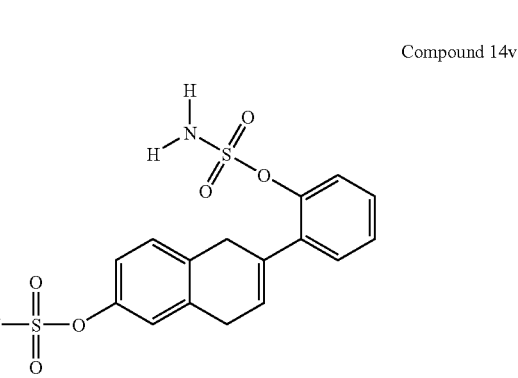
Compound 14w
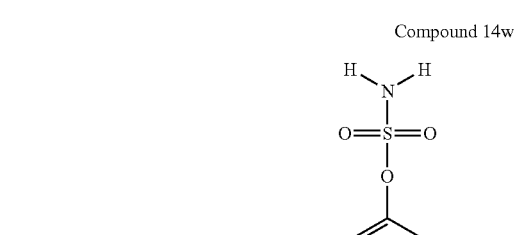
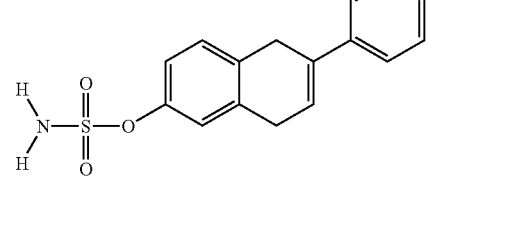

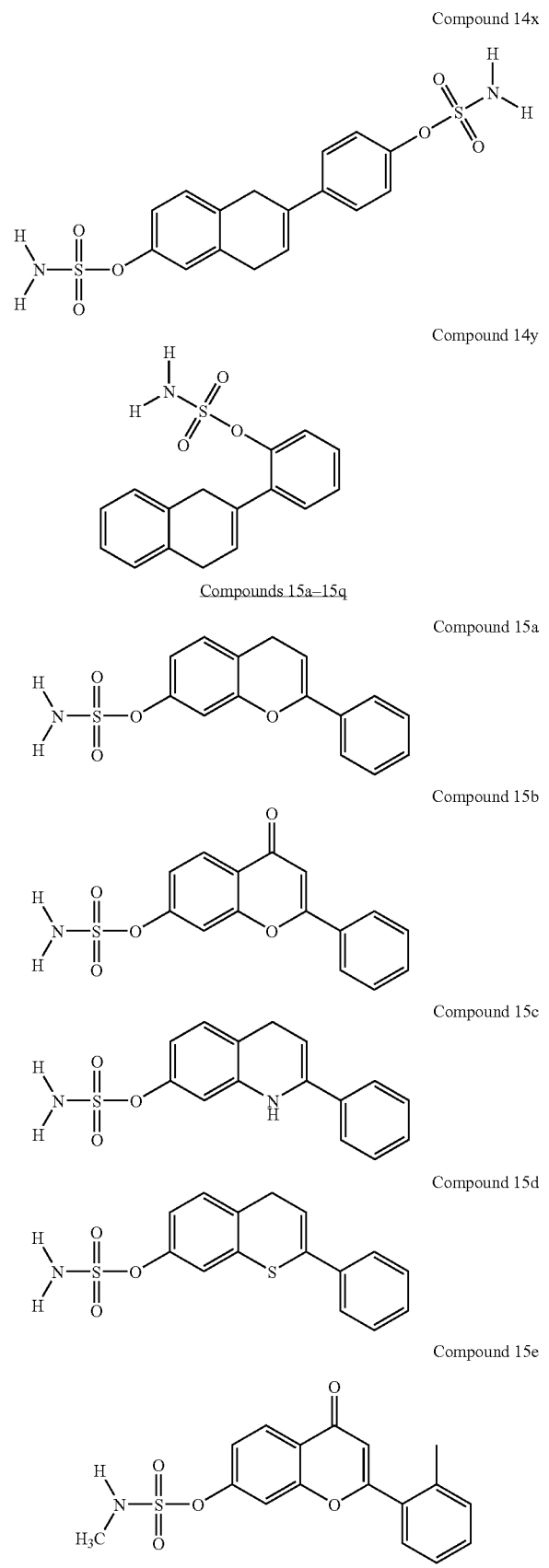
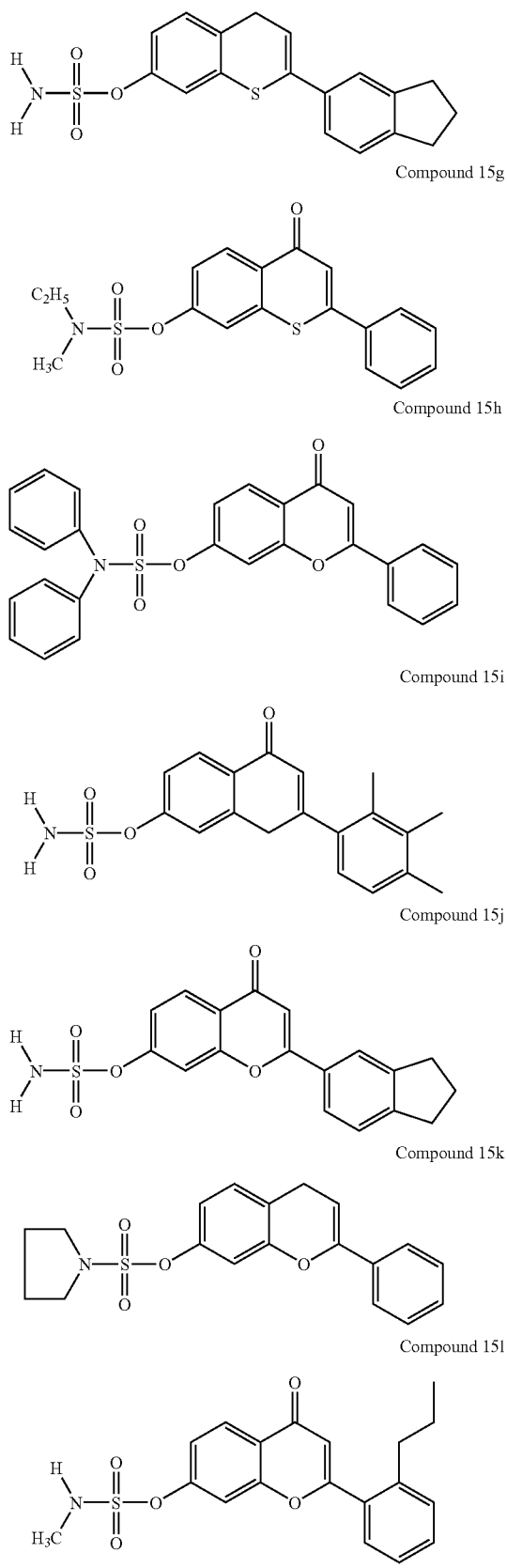

-continued

Compound 15m
Compound 15n
Compound 15o
Compound 15p
Compound 15q

Compounds 16a–16q

Compound 16a

Compound 16b
Compound 16c
Compound 16d
Compound 16e
Compound 16f
Compound 16g
Compound 16h -continued Compound 16i
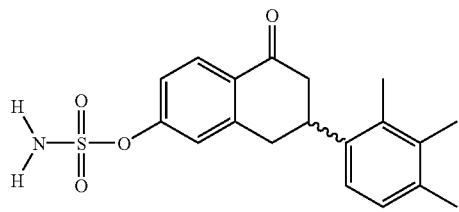

Compound 16j
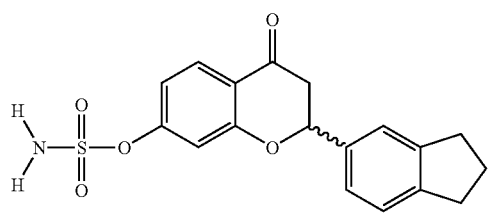

Compound 16k
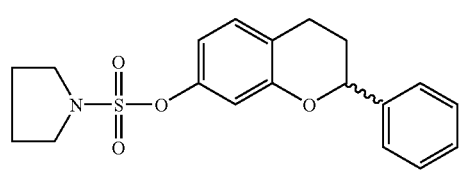

Compound 16l
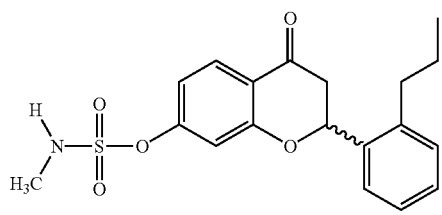

Compound 16m
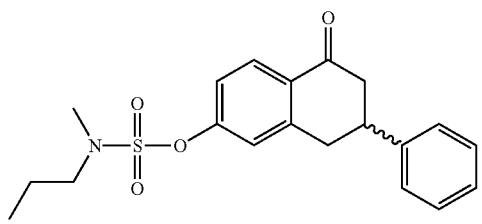

Compound 16n
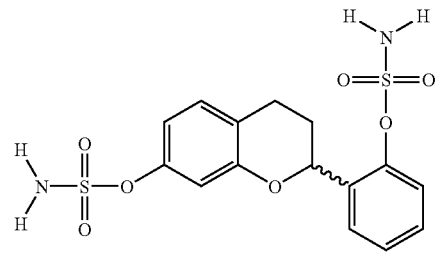

-continued

Compound 16o

Compound 16p

Compound 16q

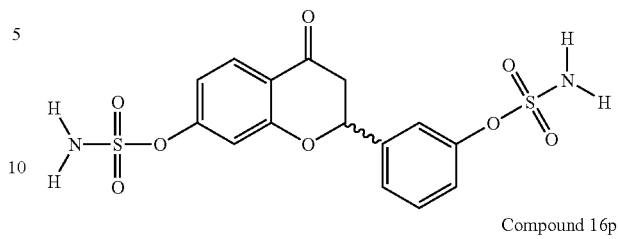

The synthesis and biological activity of further compounds in accordance with the present invention are set out in Appendix I.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

REFERENCES (1) Santner, S. J.; Feil, P. D.; Santen, R. J. In situ oestrogen production via the oestrone sulphatase pathway in breast tumors: relative importance vs. the aromatase pathway. *J. Clin. Endocrinol. Metab.* 1984, 59, 29–33.

(2) Yamamoto, T.; Kitawaki, J.; Urabe, M.; Honjo, H.; Tamura, T.; Noguchi, T.; Okada, H.; Sasaki, H.; Tada, A.; Terashima, Y.; Nakamura, J.; Yoshihama, M. Oestrogen productivity of endometrium and endometrial cancer tissue—influence of aromatase on proliferation of endometrial cancer cells. *J. Steroid Biochem. Mol. Biol.* 1993, 44, 463–468.

(3) Santen, R. J.; Santner, S. J.; Davis, B.; Veldhuis, J.; Samojilik, E.; Ruby, E. Aminogluthethimide inhibits extraglandular oestrogen production in post-menopausal women with breast carcinoma. *J. Clin. Endocrinol. Metab.* 1978 47, 1257–1265.

(4) Reed, M. J.; Lai, L. C.; Owen, A. M.; Singh, A.; Coldham, N. G.; Purohit, A.; Ghilchik, M. W.; Shaikh, N. A.; James, V. H. T. Effect of treatment with 4-hydroxy-androstenedione on the peripheral conversion of androstenedione to oestrone and in vitro tumour aromatase activity in post-menopausal women with breast cancer. *Cancer Res.* 1990, 50, 193–196.

(5) Ruder, H. J.; Loriaux, D. L.; Lipsett, M. B. Oestrone sulphate: production rate and metabolism in man. *J. Clin. Invest.* 1972, 51, 1020–1023.

(6) James, V. H. T.; McNeill, J. M.; Lai, L. C.; Newton, C. J.; Ghilchik, M. W.; Reed, M. J. Aromatase activity in normal breast and breast tumor tissues: in vivo and in vitro studies. *Steroids* 1987, 50, 269–279.

(7) Howarth, N. M.; Purohit, A.; Reed, M. J.; Potter, B. V. L. Oestrone sulphamates: potent inhibitors of oestrone sulphatase with therapeutic potential. *J. Med. Chem.* 1994, 37, 219–221.

(8) Purohit, A.; Williams, G. J.; Howarth, N. M.; Potter, B. V. L.; Reed, M. J. Inactivation of steroid sulphatase by an active site-directed inhibitor, oestrone-3-O-sulphamate.

(9) Purohit, A.; Dauvois, S.; Parker, M. G.; Potter, B. V. L.; Williams, G. J.; Reed, M. J. The hydrolysis of estrone sulphate and dehydroepiandrosterone sulphate by human steroid sulphatase expressed in transfected COS-1 cells. *J. Steroid Biochem. Mol. Biol.* 1994, 50, 101–104.

(10) Dauvois, S.; Labrie, F. Androstenedione and androst-5-ene-3β,17β-diol stimulate DMBA-induced rat mammary tumours—role of aromatase. *Breast Cancer Res. Treat.* 1989, 13, 61–69.

(11) Purohit, A.; Williams, G. J.; Roberts, C. J.; Potter, B. V. L.; Reed, M. J. In vivo inhibition of oestrone sulphatase and dehydroepiandrosterone sulphatase by oestrone-3-O-sulphamate. *Int. J. Cancer* 1995, 63, 106–111.

(12) Woo, L. W. L.; Lightowler, M.; Purohit, A.; Reed, M. J.; Potter, B. V. L. Heteroatom-substituted analogues of the active-site directed inhibitor oestra-1,3,5(10)-trien-17-one-3-sulphamate inhibit oestrone sulphatase by a different mechanism. *J. Steroid Biochem. Mol. Biol.* 1996 (in press).

(13) Elger, W.; Schwarz, S.; Hedden, A.; Reddersen, G.; Schneider, B. Sulphamates of various oestrogens—prodrugs with increased systemic and reduced hepatic oestrogenicity at oral application. *J. Steroid Biochem. Mol. Biol.* 1995, 55, 395–403.

(14) Li, P. K.; Rhodes, M. E.; Jagannathan, S; Johnson, D. A. Memory enhancement mediated by the steroid sulphatase inhibitor oestrone 3-O-sulphamate. *J. Endocrinol.* 1995, 144, Abstr. P155.

(15) Daynes, R. A.; Araneo, B. A.; Dowell, T. A.; Huang, K.; Dudley, D. Regulation of murine lymphokine production in vivo. 3. The lymphoid tissue micro-environment exerts regulatory influences over T-helper cell function. *J. Exp. Med.* 1990, 171, 979–996.

(16) Rook, G. A. W.; Hernanadez-Pando, R.; Lightman, S. Hormones, peripherally activated prohormones and regulation of the TH1/TH2 balance. *Immunol. Today* 1994, 15, 301–303.

(21) James & Reed (1980) Prog Cancer Res Ther 14: 471–487.

(22) James et al (1987) Steroids 50: 269–279.

(23) Reed et al (1994) Drugs for the Future 19: 673–680.

(24) Santner et al (1984) J Clin Endocr Metab 59: 29–33.

(25) Yamamoto et al (1993) J Steroid Biochem Molec Biol 44: 463–468.

(26) Poulin & Labrie (1986) Cancer Res 46: 4933–4937.

(27) Dauvois & Labrie (1989) Breast Cancer Res Treat 13: 61–69.

(28) Purohit et al (1994) J Steroid Biochem Mol Biol 50: 101–104.

(29) Howarth et al (1994) J Med Chem 37: 219–221.

(30) Purohit et al (1995) Biochemistry 34: 11508–11514.

(31) Purohit et al (1995) Int J Cancer 62: 106–111.

(32) Svenstrup et al (1994) Eur J Cancer 30A: 1254–1258.

(33) Johnston et al (1994) Cancer Res 54: 5875–5881.

(34) Dowsett et al (1994) Eur J Cancer 30A: 1453–1458.

(35) Kellis et al (1986) Biochem Pharmacol 35: 2887–2891.

(36) Campbell & Kurzer (1993) J Steroid Biochem Molec Biol 46: 381–388.

(37) Newton et al (1986) J Steroid Biochem 24: 1033–1039.

APPENDIX I

This appendix refers to the following figures

Figure 12:
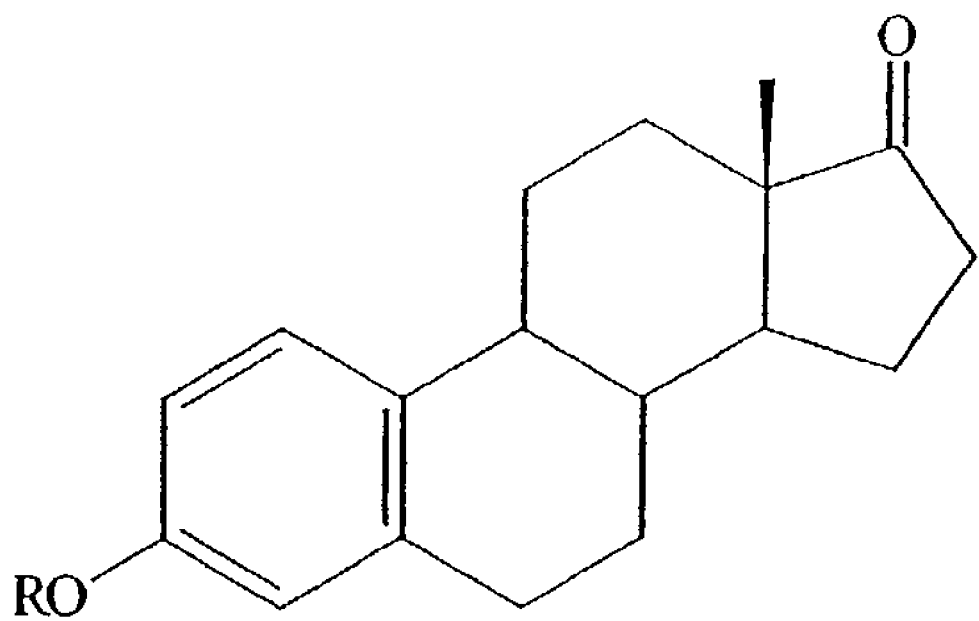
FIG. 12 presents a structure of oestrone and oestrone-3-O-sulphamate (EMATE)

FIG. 12. Structure of Oestrone and Oestrone-3-O-sulphamate (EMATE).

FIG. 13. Structure of Flavonoids.

Figure 14:
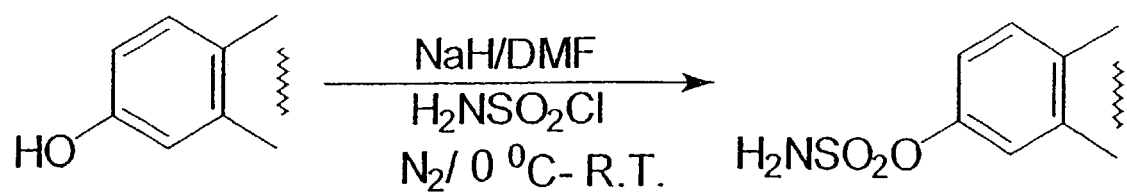
FIG. 14 presents a general method of sulphamolyation The present invention will now be described only by way of example.

FIG. 14. General Method of Sulphamolyation.

Flavonoid sulphamates 1–22 were prepared in an analogous fashion to other sulphamates described previously, as shown in FIG. 14. Briefly, a solution of the appropriate flavone, isoflavone or flavanone was treated in anhydrous DMF with sodium hydride (1.2 equiv. for monohydroxy compounds and 2.5 equiv. for dihydroxy compounds) at 0° C. (under $N_2$). Sulphamoyl chloride in toluene (excess, ca. 3 and 5 equiv. for monohydroxyl and dihydroxyl compounds respectively) was then added and after the mixture had warmed to room temperature overnight, the reaction was quenched with ethyl acetate. The crude product, after work up for each flavonoid sulphamate was purified by flash chromatography and recrystallisation. All compounds were fully characterized by spectroscopic and combustion analysis.

The yield of the sulphamates were improved significantly by using excess of sulphamoyl chloride ($\geq 5$ eq.).

Commercially unavailable (±) equol (22a) was prepared by the modified method of Wessely and Prillinger as described, and the structure was elucidated by $^1_H$NMR, $^{13}_C$NMR, Mass spectroscopy and microanalysis for the first time.

A hydroxyl group at the 5-position of the flavonoids couldn't be sulphamoylated even by using excess of NaH. This was also confirmed by attempting to sulphamoylate 5-hydroxy-7-methoxy flavone (3a). The reaction didn't work and the only explaintion is that the formation of a complex between the sodium and the ketone group at the 4-position of the flavonoids, followed by the formation of the hydrogen bond between the proton of the hydroxyl group at the 5-position and the ketone group at the 4-position of the flavonoids when the reaction was quenched, as shown by $^1$HNMR, the proton of the 5-position hydroxyl group was recorded at about 11–12 ppm (downfeild).

The stability of each sulphamate was found to be varied and influenced by different factors, such as conjugation and environmental conditions (functional groups in the sulphamate compounds, position of sulphamate group and pKa of the phenol). To establish the relationship between activity and stability, stability studies were carried out for selected flavonoid sulphamates 1, 2, 3, 16 and 20, both under the conditions of bioassay and also in methanol, using HPLC analysis. Stability studies of all flavonoid sulphamates have also been carried out in different solvents including methanol, acetone, tetrahydrofuran (THF) and ethanol using TLC.

Only the monosulphamate 20 could be obtained from 20a even by using 2.5 eq. of NaH, the bisulphamate was not formed or degraded due to lack of stability.

Biology

Inhibition of E1-STS in intact MCF-7 breast cancer cells and that of aromatase in placental microsomes by flavonoid sulphamates (1–22) is shown in Table 1.

TABLE I

Inhibition of Oestrone Sulphatase and Aromatase Activities by Flavanoid Sulphamates.

| Compound No. | % Inhibition of sulphatase activity in MCF-7 cells | | | % Inhibition of aromatase activity in placental microsomes at 10 μM. |
|---|---|---|---|---|
| | 0.1 μM | 1 μM | 10 μM. | |
| 1 | 0.30 ± 0.2 | 1.8 ± 1.0 | 4.9 ± 0.3 | 96 |
| 2 | ND | 99.1 ± 0.6 | 98.9 ± 1.3 | 14 |
| 3 | ND | 4.2 ± 0.9 | 20.6 ± 1.2 | 85 |
| 4 | 11 ± 2.7 | 51 ± 3.0 | 78 ± 1.7 | * |
| 5 | 35 ± 4.0 | 88 ± 3.1 | 99 ± 0.6 | 82 |
| 6 | * | 18 ± 6.1 | 27 ± 3.5 | 95 |
| 7 | 29 ± 0.8 | 23 ± 1.8 | 12 ± 0.5 | * |
| 8 | * | 13 ± 8.0 | 29 ± 1.3 | * |
| 9 | 8 ± 2.6 | 79 ± 0.8 | 98 ± 0.4 | 90 |
| 10 | * | 8 ± 6.4 | 12 ± 7.5 | 14 |
| 11 | * | * | * | * |
| 12 | * | * | * | 39 |
| 13 | * | * | * | 38 |
| 14 | * | * | * | 22 |
| 15 | * | * | * | 35 |
| 16 | * | 11 ± 3.0 | 37 ± 1.7 | * |
| 17 | 28 ± 1.7 | 90 ± 0.6 | 99 ± 1.4 | * |
| 18 | 23 ± 2.2 | 83 ± 2.7 | 99 ± 0.7 | * |
| 19 | 87 ± 2.5 | >99 | >99 | * |
| 20 | 30 ± 2.8 | 79 ± 1.2 | 98 ± 1.2 | 85 |
| 21 | 2 ± 1.3 | 8 ± 0.6 | 9 ± 1.2 | 60 |
| 22 | >99 | >99 | >99 | 13 |
| 23 | * | * | * | ND |
| 24 | 18.4 ± 0.8 | 42.2 ± 1.3 | 95.3 ± 0.3 | ND |
| 25 | 14.9 ± 7 | 65.4 ± 1.2 | 96.2 ± 0.2 | ND |
| 26 | 99.6 ± 0.3 | 99.6 ± 0.4 | 99.1 ± 0.1 | ND |

ND: not determined
*Inactive

TABLE 2

Inhibition of oestrone Sulphatase in vivo for Flavanoid Sulphamates and EMATE as measured in rat liver, 24 hours after single oral dose in propylene glycol.

| NO. | Compound | Dosage | % Inhibition |
|---|---|---|---|
| 1b | EMATE | 1 mg/Kg | >99 |
| 17 | 5-Hydroxy isoflavone-4',7-O,O-bisulphamate | 10 mg/Kg | 81.4 ± 3.2 |
| 18 | 5,7-Dihydroxy-4'-O-sulphamate | 10 mg/Kg | 62.0 ± 4.7 |
| 19 | Isoflavone-4',7-O,O-bisulphamate | 10 mg/Kg | 71.4 ± 2.9 |
| 20 | 5,7-Dihydroxy flavanone-4'-O-sulphamate | 10 mg/Kg | 44.2 ± 3.8 |

The results can be summarized as follows: Most of these compounds significantly inhibited E1-STS in MCF-7 cells when added at a concentration of 10 μM. Compounds 17–20 are the most active in this series, with inhibitory activity about 99% in MCF-7 cells at 10 μM. However, in general, it was found that the isoflavone sulphamates 17–19 are more potent than flavone and flavanone sulphamates. It was also found that bisulphamates are more potent than the corresponding monosulphamate (e.g. 17 and 18).

The effect of a sulphamate group when attached to a non-aromatic ring (ring C of flavonoids) was also evaluated and found to be inactive (10–15), confirming that the phenyl ring structure is required for potent inhibition.

Discussion

In the last ten years, numerous reports have suggested the importance of oestrone sulphate and oestrone sulphatase in regulating the supply of oestrogens to oestrogen-dependent breast cancer. Thus, E1-STS inhibitors may prove to be useful for the treatment of breast cancers. We have already demonstrated that EMATE 1b is the most potent active-site directed irreversible inhibitor reported to date. However, due to the oestrogenic activity of EMATE there remains a real and substantial need for potent non-steroidal E1-STS inhibitors that are metabolically stable, more selective and devoid of oestrogenic activity.

Having identified the key chemical structural requirement for potent sulphatase inhibition (i.e. phenolic ring structure and —O-sulphamoyl group), we considered that introduction of the sulphamoyl group into the flavonoids structure might significantly engender sulphatase inhibitory activity and, might provide new lead for the design of a dual non-steroidal sulphatase/aromatase inhibitor as several flavonoids have aromatase inhibitory activity (REFs). We selected the flavonoid system for the following reasons: 1) Since EMATE is highly oestrogenic, there is a need to develop other classes of potential inhibitors. 2) Flavonoids are ubiquitous commercially available secondary plant metabolites and possess not only a phenolic ring structure (one of a key chemical structural requirements for potent sulphatase inhibition), which can potentially mimic the A ring of EMATE, but another phenyl ring which can also be (poly) hydroxylated. 3) Flavonoids are natural compounds, the vast majority of them are nontoxic to human and animals, and the known pharmacological activities are limited to a few substances of this group. 4) The low rate of incidence of breast cancer in the Far East, rather than genetic difference is an important factor, has been related to a high dietary intake of Soya products containing flavones and isoflavones. 5) It has been reported that several flavonoids are potent aromatase inhibitors and it is likely that sulphamates of these flavonoids will also inhibit the activity of this enzyme. 6) Recently it has also been reported that some flavonoids inhibited the enzyme 17β-hydroxysteroid dehydrogenase which converts oestrone to oestradiol the most biologically active oestrogen.

and 7) We have shown that the related coumarin ring system when sulphamoylated, can possess good E1-STS inhibition activity (REF).

Biological evaluation of the novel synthetic entities revealed that most of these flavonoid sulphamates (1–22) show potent sulphatase inhibitory properties at 10 μM in MCF-7 cells. Compounds (5, 17, 18 and 20) inhibited E1-STS in MCF-7 cells in ranges of 22–87% at 0.1 μM, 79–99% at 1 μM and >99% at 10 μM. The best inhibitor in this series, isoflavone-4',7-O,O-bisulphamate (19), inhibited E1-STS activity in MCF-7 cells by 87% and >99% at 0.1 μM and 1 μM respectively.

Flavone-7-O-sulphamate, (1) was found to inhibit aromatase in placental microsomes by 86% at 10 μM. This result is encouraging as our approach of synthesizing flavonoid sulphamates may lead to the eventual development of dual aromatase/sulphatase inhibitors. However, we need to establish in future work if the inhibition of aromatase by (1) is actually an inherent property of the molecule or is the result of an in vivo activation of (1) to the potent known aromatase inhibitor, 7-hydroxyflavone (1c).

Many sulphamates were noticed to be only weakly stable or unstable at high temperature and in the more polar solvents and decomposed in DMF (reaction solvent). Therefore, by using a larger excess of sulphamoyl chloride (±5 eq.) than used the yield improved significantly.

However, to understand and imporve the relationship between the activity and stability of flavonoid sulphamates, stability studies were carried out by HPLC for some selective flavonoid sulphamates under the same conditions of biological assay and in methanol, and also by TLC in different solvents including methanol, acetone, tetrahydrofuran (THF) and ethanol. The following general results were noticed:

i) Most of the conjugated sulphamates (double bond in ring C of flavonoids structure) were unstable and decomposed quickly to their parent compounds in the biological medium and methanol.

ii) The presence of functional groups such as methoxy group, hydroxy group and ketone group on the main ring of the sulphamates structure increases the degradation of these compounds.

iii) The sulphamates were found to be weakly stable and decomposed slowly in acetone, but unstable and decomposed rapidly in methanol, ethanol, and DMSO. Most of the sulphamates were fairly stable in THF. Therefore, it is advisable when possible to use THF to dissolve the compound for biological assay to avoid potential degradation.

iv) All bis-sulphamates were found to be fairly stable in solvents and in the biological medium and they decomposed to corresponding monosulphamate parent compounds (e.g. 17, 18).

v) It was found that when the sulphamoyl group was present at the 6-position of flavonoid sulphamates, the sulphamates were more stable than if it was present at 7-position, e.g. flavone-6-O-sulphamate 2 is more stable than flavone-7-O-sulphamate 1. It also was found that when the sulphamoyl group was present at the 4'-position of flavonoid sulphamates it is more stable than if it is at 7-position. For example, 5,7-dihydroxy flavanone-4'-O-sulphamate 20 is more stable and has significant activity compared with the 7-O-sulphamates of flavonoids.

It was noticed that the stable sulphamates established significant activity, while the unstable compounds in the main show moderate or no activity.

These stability studies were able to guide us to introduce the sulphamoyl group at the most favorable position of flavonoids with respect to stability (i.e. 4' of ring B of flavonoids structure) of sulphatase and aromatase inhibitors. We believe that the ketone group and the conjugation in ring C of flavonoids play major roles in reducing the stability, which affects negatively the inhibition of E1-STS activity. Therefore, to confirm this and to improve the stability of the potent isoflavone sulphamates (17–19), we have synthesized (±) 4',7-dihydroxy flavane (equol) 22a and sulphamolyated it to get isoflavane 4',7-O,O-bisulphamate 22 (22a was first recognized in 1932; our study is the first to provide modern spectroscopic data for this compound). This compound was found to be more stable in polar solvents than the corresponding isoflavone-4',7-O,O-bisulphamate 19 as shown by a TLC study, but it is less potent for inhibition of E1-STS activity in MCF-7 and placental microsomes. Thus, we can say now that the presence of the ketone group at the 4-position of ring C in the flavonoid structure decreases stability but it is nevertheless essential for potent E1-STS inhibition activity, perhaps by contributing extra binding to the active site of the enzyme.

Further modifications need to be carried out in this series to improve both sulphatase and aromatase inhibitory activities significantly and to make the usually compounds completely devoid of oestrogenic activity, as it is known that some flavonoids are oestrogenic at high dose (REF).

Overall, this study has revealed that flavonoid sulphamates are a new class of potential E1-STS inhibitors and can establish significant inhibition of E1-STS activity. We have also provided preliminary evidence supporting the concept and novel idea of a dual sulphatase/aromatase inhibitor based upon the flavonoid system. More work is required to explore this goal, but some of the compounds reported here could be useful new leads.

CONCLUSION

This study has clearly demonstrated that the sulphamoyl group is essential for E1-STS inactivation, as most of these flavonoid sulphamates are potent and significantly inhibited E1-STS in MCF-7 cells when present at 10 µM or lower. Our data indicate that flavonoid sulphamates 2, 5, 9, 17–20 and 22 are potent sulphatase inhibitors which also possess aromatase inhibitory activity. These compounds therefore represent key lead compounds for optimization of potential dual sulphatase/aromatase inhibitors.

Flavonoid sulphamates may therefore be effective therapeutic agents in the treatment of oestrogen-dependent breast cancer, but it is crucial to be fully cognizant of inherent stability problems.

This observation opens the door for further studies to design and maximize metabolically stable potent dual sulphatase/aromatase inhibitors.

Experimental Section

Materials, Methods and Instruments Used

Chemistry

All reagents and solvents employed were of general purpose or analytical grade used without purification unless otherwise stated, and purchased from either Aldrich Chemicals or Lancaster Synthesis. Silica gel refers to silica gel 60, 230–400 mesh (MercK), and analytical TLC was performed on pre-coated plates (Merck TLC, aluminium sheets silica $F_{254}$. Art No. 5554) with detection by either UV light or using methanolic phosphomolybdic acid followed by heating. All Melting points were determined on Reichert-Jung Kofler block and are uncorrected. Microanalysis were performed with a Carlo Erba elemental analyzer (Model 1106) for C, H, N, IR, spectra were determined using KBr discs, using a Perkin-Elmer 782 Infra-Red Spectrophotometer and are expressed in $cm^{-1}$. The $^1$HNMR spectra were recorded on a Jeol GX 270 at 270 MHz and on a Jeol EX 400 at 400 MHz; chemical shifts are reported in part per million (ppm) on the δ scale downfield relative to trimethylsilane as internal standard; coupling constants (J) are reported in hertz (Hz). The following abbreviations are used to describe resonances in $^1$HNMR spectra, s=singlet; d=doublet; T=triplet; q=quartet; m=multiplet; br=broad and combination such as dd=doublet of doublets.

Mass spectra were recorded on VG 7070 and VG Autospec instruments. HPLC Stability studies were determined using LDC Constametric 3000 HPLC Pump and Spectrometer 3000 variable wave length detector.

All reagents and solvents used were stored away from moisture and light and dried before use. All organic extracts were dried over $MgSO_4$. Evaporation implies the removal of solvents by use of a rotary evaporator at 30–35° C. under vacuum (water pump) and on stated occasions, followed by the use of a high vacuum pump. The samples were dried in a drying tube at low temperature at reduced pressure.

Microanalysis were determined at the University of Bath

Stability Study by HPLC

A small amount of sulphamate was taken and dissolved in 1 ml methanol. Sulphamate methanolic solution (10%) was prepared by dissolving 100 µl of this solution in 900 µl phosphate buffer solution (PBS) at 37° C. The resulting solution was injected immediately into an HPLC. Samples were injected at 0, 5, 10, 20, 30, 60 and 120 min. (depending upon rate of degradation of sulphamate, the injection time was varied). The mobile phase used was 90%, 70%, 30% and 10%, but in recent studies 10% of methanol was used, and a low concentration of methanol as mobile phase (10%) is advisable to avoid the possibility of degradation of sulphamates by methanol. The flow rate was 1 ml/min. To select the optimum wavelength of absorptions by different sulphamates, the UV scan was checked between 200–350 nm. The wavelength of EMATE type compounds was at 270 nm.

As the amount of sample is not known accurately, sensitivity on integrator or recorder is by trial and error.

Preparation of Sulphamoyl Chloride

Sulphamoyl chloride was prepared by the reaction of chlorosulphonyl isocyanate with formic acid according to the method of Appel and Berger. To anhydrous sulphur-free toluene (150 ml) chlorosulphonyl isocyanate (25 g., 177 mmol) was added at 0° C. under an atmosphere of $N_2$. After stirring, formic acid (6.0 ml, 156 mmol) was added dropwise at 0° C. under $N_2$. The resulting white light emulsion was kept stirring overnight and the toluene removed by using a water vacuum pump to give a light yellow crude of sulphamoyl chloride (16.24 g, 79%). A standard solution (0.70 M) of sulphamoyl chloride was then prepared by dissolving the crude crystalline product in anhydrous sulphur-impurities-free toluene and stored in the dark under $N_2$.

Toluene used for preparing sulphamoyl chloride solution was purified according to the method described. Cold toluene (1–3 liters) was placed in a separating funnel and washed with cold conc. $H_2SO_4$ (100 ml/liters, 3–4 times), once with water, once with aqueous 5% NaOH and again with water until neutral, dried with anhydrous $MgSO_4$ and sodium metal overnight and then fractionally distilled under $N_2$ from sodium metal and stored in dark under $N_2$.

Anhydrous formic acid used for preparing sulphamoyl chloride was purified according the method described. Formic acid (98%) was stirred overnight with boric anhydride and then distilled under $N_2$, stored in dark under $N_2$, and for further purification, fractional crystallization using partial freezing was used.

General Synthesis of Flavonoid Sulphamates (1–22)

Starting with the parent compound, the sulphamate derivatives were prepared essentially as previously described (FIG. 13). In this regard, a solution of the appropriate flavone I, isoflavone II or flavanone III in anhydrous DMF was treated with sodium hydride [60% dispersion; 1.2 and 2.5 equiv. for monohydroxyl and dihydroxyl compounds respectively] at 0° C. under an atmosphere of $N_2$. After evolution of hydrogen had ceased, sulfamoyl chloride in toluene [excess, ca. 3 and 5 equiv. for monohydroxyl and dihydroxyl compounds respectively] was added and the reaction mixture was poured into brine after warming to room temperature overnight and diluting with ethyl acetate. The organic fraction was washed exhaustively with brine, dried ($MgSO_4$), filtered and evaporated. The crude product obtained was purified by flash chromatography and recrystallisation to give the corresponding sulfamate. All the compounds were fully characterized by spectroscopic and combustion analysis.

Flavone-7-O-sulphamate (1)

7-Hydroxyflavone (500 mg, 2.098 mmol) gave a light yellow residue (606 mg) of which 393 mg in silica (7 g) was fractionated on silica (400 g) with ethyl acetate. Upon evaporation of the first fraction collected gave a white residue (168 mg, 529.4 µmol, 39%) which was recrystallized in ethyl acetate/hexane (1:1) to give () as white crystals (91 mg); m.p.=173° C., the yellow oil formed gave crystals which melted at 210–220° C. (c.f. 7-hydroxyflavone, m.p.=245–247° C.); $R_fs$=0.78 (ethyl acetate) and 0.56 (ethyl acetate/hexane, 4:1); vmax (KBr) 3250, 3080, 1620, 1590, 1390, 1190 cm$^{-1}$; $\delta_H$ (400 MHz, acetone-$d_6$) 6.89 (1H, s, C-3-H), 7.42 (1H, dd, $J_{C-8-H, C-6-H}$=2.4 Hz and $J_{C-5-H, C-6-H}$=8.7 Hz, C-6-H), 7.45 (2H, br s, exchanged with $D_2O$, $OSO_2NH_2$), 7.61 (3H, m, Ar—H of B-ring), 7.72 (1H, d, $J_{C-6-H, C-8-H}$=2.1 Hz, C-8-H), 8.10 (2H, m, Ar—H of B-ring) and 8.17 (1H, d, $J_{C-6-H, C-5-H}$=8.5 Hz, C-5-H). MS: m/z (+ve ion FAB, rel. intensity) 318.0 [100, $(M+H)^+$], 255.2(28), 239.1 [20, $(M+2H-SO_2NH_2)^+$], 173.2(47), 93.9 (32). MS: m/z (–ve ion FAB, rel. intensity) 483.1(30), 468.1 [10, $(M-2H+NBA)^-$], 316.0 [100, $(M-H)^-$], 237.1 [30, $(M-SO_2NH_2)^-$]. Acc. MS: m/z 318.04455, $C_{15}H_{12}NO_5S$ requires 318.04362. Found: C, 56.5; H, 3.44; N, 4.29. $C_{15}H_{11}NO_5S$ requires C, 56.78; H, 3.49; N, 4.41%.

Flavone-6-O-sulphamate (2) and adduct (O)

6-Hydroxyflavone (1.0 g, 4.113 mmol) gave a yellow residue (1.21 g) which was recrystallized in acetone/hexane (3:2) to give (2) as creamy crystals (557 mg). The residue (460 mg) from the mother liquor was fractionated on silica (100 g) with ethyl acetate and upon evaporation of the first fraction collected gave a creamy residue (234 mg, total yield=2.493 mmol, 61%) which was recrystallized in acetone/hexane (2:1) to give a second crop of (2) as white crystals (87 mg); m.p.=190–192° C.; $R_fs$=0.71 (ethyl acetate) and 0.51 (ethyl acetate/hexane, 2:1); vmax (KBr) 3260, 3040, 1620, 1580, 1370, 1180 cm$^{-1}$; $\delta_H$ (270 MHz, acetone-$d_6$) 6.92 (1H, s, C-3-H), 7.36 (2H, br s, exchanged with $D_2O$, $OSO_2NH_2$), 7.64 (3H, m, Ar—H of B-ring), 7.75 (1H, dd, $J_{C-5-H, C-7-H}$=3 Hz and $J_{C-8-H, C-7-H}$=9 Hz, C-7-H), 7.87 (1H, d, $J_{C-7-H, C-8-H}$=9 Hz, C-8-H), 8.02 (1H, d, $J_{C-7-H, C-5-H}$=3 Hz, C-5-H) and 8.13 (2H, m, Ar—H of B-ring). MS: m/z (E.I., 70 eV, rel. intensity) 317.0(11, $M^+$), 304.2(6), 238.0 [96, $(M+H-SO_2NH_2)^+$], 210.0(16), 187.1 (14), 136.0(100), 108.0(26). Acc. MS: m/z 317.02959, $C_{15}H_{11}NO_5S$ requires 317.03579. Found: C, 56.7; H, 3.44; N, 4.31. $C_{15}H_{11}NO_5S$ requires C, 56.78; H, 3.49; N, 4.41%.

The third fraction collected upon evaporation gave a creamy residue (38 mg) which was recrystallized in acetone/hexane (1:1) to give (()) as creamy crystals (17 mg); m.p. 198–199° C.; $\delta_H$ (270 MHz, acetone-$d_6$) 3.09 (3H, s, NCH$_3$), 3.28 (3H, s, NCH$_3$), 6.91 (1H, s, C-3-H), 7.63 (3H, m, Ar—H of B-ring), 7.71 (1H, dd, $J_{C-5-H, C-7-H}$=3 Hz and $J_{C-8-H, C-7-H}$=9 Hz, C-7-H), 7.83 (1H, d, $J_{C-7-H, C-8-H}$=9 Hz, C-8-H), 7.97 (1H, d, $J_{C-7-H, C-5-H}$=3 Hz, C-5-H) and 8.13

(3H, m, —CH=N— and Ar—H of B-ring). Found: C, 58.0; H, 4.32; N, 7.39. $C_{18}H_{16}N_2O_5S$ requires C, 58.06; H, 4.33; N, 7.52%.

5-Hydroxyflavone 7-O-sulphamate (3)

5,7-Dihydroxyflavone (1.0 g, 3.933 mmol) gave crude product (1.13 g) which was fractionated on silica (200 g) with chloroform/acetone (8:1). Upon evaporaton, the second fraction gave a yellow residue (0.324 g, 24%) which was recrystallised in ethyl acetate/hexane (1:1) to give 3 as yellow crystals (0.213 g), m.p. 195–200° C. (dec.); $R_f$s=0.21, 0.25 and 0.44 for chloroform/acetone 12:1, 8:1 and 4:1 respectively; vmax (KBr) 3360 ($NH_2$), 1650 (C=O), 1380 (—$SO_2N$—) cm.$^{-1}$. $\delta_H$ (acetone-$d_6$.) 6.75, 6.98 and 7.17 (3H, three s, C-3-$\underline{H}$, C-6-$\underline{H}$, C-8-$\underline{H}$), 7.63 (2H, br s, exchanged with $D_2O$, —$OSO_2N\underline{H}_2$), 7.65 (3H, m, C-3'-$\underline{H}$, C-4'-$\underline{H}$ and C-5'-$\underline{H}$), 8.15 (2H, d, J=7.7 Hz, C-2'-$\underline{H}$ and C-6'-$\underline{H}$) and 13.0 (1H, br s, C-5-O$\underline{H}$). MS: m/z (+ve ion FAB in m-NBA, rel. intensity) 334.1 [100, $(M+H)^+$], 255.0 [25, $(M+H-SO_2NH_2)^+$], MS: m/z (-ve ion FAB in m-NBA, rel. intensity) 484.1 [14, $(M-H+153 (m-NBA))^-$], 332.1 [100, $(M-H)^-$], 253.1 [50, $(M-H-SO_2NH_2)^+$]. Acc. MS (+ve ion FAB in m-NBA): m/z 334.0392, $C_{15}H_{12}NO_6S$ requires 334.0385. Found: C, 54.0; H, 3.39; N, 4.21. $C_{15}H_{11}NO_6S$ requires C, 54.03; H, 3.33; N, 4.20%.

5-Hydroxy-7-methoxy flavone-6-O-sulphamate (4)

5,6-Dihydroxy-7-methoxy flavone (0.5 g, 1.760 mmol) gave a crude product (0.68 g) which was fractionated on silica (200 g) with chloroform/acetone (8:1), and upon evaporation the second fraction gave a yellow residue (0.463 g, 68%) which was recrystallized in acetone/hexane (1:2) to give 4 as yellow crystals (0.347 g); m.p. 209–212° C.; $R_f$s=0.13, 0.33 and 0.65 for chloroform/acetone 8:1, 4:1 and 2:1 respectively; vmax (KBr) 3380 (—$NH_2$), 3200 (H-bonded —OH), 1720 (C=O), 1380 (—$SO_2N$—), cm$^{-1}$; $\delta_H$ (DMSO-$d_6$) 3.95 (3H, s, C-7-OC$\underline{H}_3$), 7.07 (1H, s, C-3-$\underline{H}$ or C-8-$\underline{H}$), 7.12 (1H, s, C-8-$\underline{H}$ or C-3-$\underline{H}$), 7.12 (3H, d, J=7.3 Hz, C-3'-$\underline{H}$, C-4'-$\underline{H}$, C-5'-$\underline{H}$), 7.84 (2H, s, exchanged with $D_2O$, —$OSO_2N\underline{H}_2$), 8.13 (2H, d, J=7.0 Hz, C-2'-$\underline{H}$ and C-6'-$\underline{H}$) and 13.06 (1H, s, C-5-$\underline{H}$). MS: m/z (+ve ion FAB in m-NBA, rel. intensity) 364.0 [100, $(M+H)^+$], 284.1 [40, $(M+H-SO_2NH_2)^+$]. Acc. MS: m/z $(FAB)^+$ 364.0511 $C_{16}H_{14}NO_7S$ requires 364.0491. Found C, 52.5; H, 3.68; N, 3.66; $C_{16}H_{13}NO_7S$ requires C, 52.89; H, 3.61; N, 3.85%.

5-Hydroxy-7-methoxy-flavone-4'-O-sulphamate (5)

4',5-Dihydroxy-7-methoxy flavone (75 mg, 0.264 mmol) gave a crude product (112 mg) which was fractionated on silica (50 g) with chloroform/acetone (8:1), and upon evaporation the second fraction gave a yellow residue (76.5 mg, 68%) which was recrystallized in ethylacetate/hexane (1:2) to give 5 as yellow crystals (55 mg); m.p.=189–192° C.; $R_f$s=0.16 and 0.26 for chloroform/acetone 8:1 and 4:1 respectively, vmax (KBr) 3500 (—$NH_2$), 3300 (H-bonded —OH), 1660 (C=O), 1380 (—$SO_2N$—), cm$^{-1}$. $\delta_H$ (acetone-$d_6$) 3.94 (1H, s, C-7-OC$\underline{H}_3$), 6.36 (1H, d, J=2.5 Hz, C-6-$\underline{H}$ or C-8-$\underline{H}$), 6.73 (1H, d, J=2.2 Hz, C-8-$\underline{H}$ or C-6-$\underline{H}$), 6.84 (1H, s, C-3-$\underline{H}$) 7.35 (2H, br s, exchanged with $D_2O$, —$SO_2N\underline{H}_2$), 7.54 (2H, d, J=8.8 Hz, C-3'-$\underline{H}$ and C-5'-$\underline{H}$ or C-2'-$\underline{H}$ and C-6'-$\underline{H}$), 8.18 (2H, d, J=8.8 Hz, C-2'-$\underline{H}$ and C-6'-$\underline{H}$ or C-3'-$\underline{H}$ and C-5'-$\underline{H}$) and 12.81 (1H, s, C-5-O$\underline{H}$). MS: m/z (+ve ion FAB in m-NBA, rel. intensity) 364.0 [100, $(M+H)^+$], 285.1 [15, $(M+H-SO_2NH_2)^+$]. MS: m/z (-ve ion FAB in m-NBA, rel. intensity) 361.9 [95, $(M-H)^-$], 283.0 [100, $(M-H-SO_2NH_2)^-$]. Acc. MS: m/z $(FAB^+)$=364.0500 $C_{16}H_{14}NO_7S$ requires 364.0491 Found C, 51.1; H, 3.69; N, 3.73; $C_{16}H_{13}NO_7S$ requires C, 52.89; H, 3.61; N, 3.85%.

5-Hydroxy 4',6,7-Trimethoxy flavone-3'-O-sulphamate (6)

3',5-Dihydroxy-4',6,7-trimethoxy flavone (75 mg, 0.177 mmol) gave a crude product (103 mg) which was fractionated on silica (50 g) with chloroform/acetone (4:1), and upon evaporation the second fraction gave a yellow residue (58 mg, 56%) which was recrystallized in ethylacetate/hexane (1:2) to give 6 as yellow crystals (32 mg); m.p. 197–199° C.; $R_f$s=0.175 and 0.44 for chloroform/acetone 4:1 and 2:1 respectively; vmax (KBr) 3360 (—$NH_2$), 3260 (H-bonded —OH), 1620 (C=O), 1370 (—$SO_2N$—) cm$^{-1}$; $\delta_H$ [DMSO-$d_6$/CDCl$_3$, (1:5)] 3.88 (3H, s, C-4'-OC$\underline{H}_3$), 3.986 (6H, d, J=4.8 Hz, C-6-OC$\underline{H}_3$ and C-7-OC$\underline{H}_3$), 6.66 (1H, s, C-3-$\underline{H}$ or C-8-$\underline{H}$), 6.71 (1H, s, C-8-$\underline{H}$ or C-3-$\underline{H}$), 7.16 (1H, d, J=8.8 Hz, C-5'-$\underline{H}$), 7.63 (2H, s, exchanged with $D_2O$, —$OSO_2N\underline{H}_2$), 7.86 (1H, d, J=8.8 Hz, C-6'-$\underline{H}$), 7.97 (1H, d, J=2.2 Hz, C-2'-$\underline{H}$) and 12.74 (1H, s, C-5-O$\underline{H}$). MS: m/z (+ve ion FAB in m-NBA, rel. intensity) 424.1 [100, $(M+H)^+$], 344.1 [10, $(M-SO_2NH_2)^+$]. MS: m/z (-ve ion FAB in m-NBA, rel. intensity) 422.1 [100, $(M-H)^-$], 344.1 [20, $(M-SO_2NH_2)^-$]. Acc. MS: m/z $(FAB)^+$ 424.0714 $C_{18}H_{18}NO_9S$ requires 424.0702. Found C, 51.1; H, 3.38; N, 4.33; $C_{18}H_{17}NO_9S$ requires C, 51.06; H, 3.31; N, 4.05%.

4',5,6,7-Tetramethoxy flavone-3'-O-sulphamate (7)

3'-Hydroxy-4',5,6,7-tetramethoxy flavone (75 mg, 0.210 mmol) gave a crude product (96 mg) which was fractionated on silica (50 g) with chloroform/acetone (4:1), and upon evaporation the second fraction gave a yellow residue (59 mg, 62%) which was recrystallized in ethylacetate/hexane (1:2) to give 7 as yellow crystals (35 mg); m.p. 138–141° C.; $R_f$s=0.10, 0.27 and 0.59 for chloroform/acetone 8:1, 4:1 and 2:1 respectively; vmax (KBr) 3420 (—$NH_2$), 1640 (C=O), 1380 (—$SO_2N$—) cm$^{-1}$; $\delta_H$ (acetone-$d_6$) 3.93 (12H, m, C-5-OC$\underline{H}_3$, C-6-OC$\underline{H}_3$, C-7-OC$\underline{H}_3$, and C-4'-OC$\underline{H}_3$), 6.55 (1H, s, C-3-$\underline{H}$) 7.13 (1H, s, C-8-$\underline{H}$), 7.23 (2H, br s, exchanged with $D_2O$, —$OSO_2N\underline{H}_2$) 7.24 (1H, d, J=8.4 Hz, C-5'-$\underline{H}$) and 7.93 (2H, m, C-2'-$\underline{H}$ and C-6'-$\underline{H}$). MS: m/z (+ve ion FAB in m-NBA, rel. intensity) 437.9 [100, $(M+H)^+$], 359.0 [10, $(M+H-SO_2NH_2)^+$]. MS: m/z (-ve ion FAB in m-NBA, rel. intensity) 436.0 [100, $(M-H)^-$], 357.0 [10, $(M-H-SO_2NH_2)^-$]. Acc. MS: m/z $(FAB)^+$ 438.0866 $C_{19}H_{20}NO_9S$ requires 438.0859. Found C, 51.5; H, 3.18; N, 4.46; $C_{19}H_{19}NO_9S$ requires C, 52.17; H, 3.20; N, 4.38%.

Flavone-3',4'-O,O-bisulphamate (8)

3',4'-dihydroxy flavone (0.45 g, 1.77 mmol) gave a crude product (0.763 g) which was fractionated on silica (200 g) with ethyl acetate/acetone/hexane (2:1:1), and upon evaporation the second fraction gave a pale residue (0.376 g, 49%), which was recrystallized in acetone/hexane (1:2) to give 6 as white crystals (0.173 g); m.p. 170–172° C.; $R_f$s=0.7 and 0.51 for ethyl acetate/acetone 2:1 and ethyl acetate/acetone/hexane 2:1:1 respectively; vmax (KBr) 3240 (—$NH_2$), 1630 (C=O), 1390 (—$SO_2N$—) cm$^{-1}$; $\delta_H$ [DMSO-$d_6$/CDCl$_3$ (1:3)] 6.91 (1H, s, C-3-$\underline{H}$), 7.47 (1H, t, J=7.5 Hz, C-6-$\underline{H}$) 7.65 (1H, d, J=8.4 Hz, C-6'-$\underline{H}$), 7.72 (1H, s, C-8-$\underline{H}$), 7.75 (1H, d, J=5.9 Hz, C-7-$\underline{H}$), 7.92 (1H, s, C-5-$\underline{H}$), 7.97 (4H, br s, exchanged with $D_2O$, C-3'-$OSO_2N\underline{H}_2$ and C-4'-$OSO_2N\underline{H}_2$), and 8.15 (2H, d, J=7.7 Hz, C-2'-$\underline{H}$ and C-5'-$\underline{H}$). MS: m/z (+ve ion FAB in m-NBA, rel. intensity) 413.1 [100, $(M+H)^+$], 334.1 [20, $(M+H-SO_2NH_2)^+$], 254.1 [20, $(M-SO_2NH_2)^+$]. MS: m/z (-ve ion FAB in m-NBA, rel. intensity) 411.0 [100, $(M-H)^-$], 332.1 [35, $(M-H-SO_2NH_2)^-$], 253.1 [40, $(M-H-SO_2NH_2)^-$]. Acc. MS: m/z 413.0120 $C_{15}H_{13}N_2O_8S_2$ requires 413.0113. Found C, 44.3; H, 3.3; N, 6.21; $C_{15}H_{12}N_2O_8S_2$ requires C, 43.69; H, 2.93; N, 6.79%.

5-Hydroxy flavone-4',7-O,O-bisulphamate (9)

4',5,7-Trihydroxy flavone (72 mg, 0.266 mmol) gave a crude product (117 mg) which was fractionated on silica (50 g) with chloroform/acetone (2:1) and upon evaporation the second fraction gave a yellow residue (70 mg, 60%) which was recrystallized in acetone/chloroform (1:2) to give 9 as yellow crystals (45 mg); m.p.>198° C. (dec.); $R_f$s=0.083 and 0.385 for chloroform/acetone 4:1 and 2:1 respectively; vmax (KBr) 3380 (—$NH_2$), 3260 (H-bonded —OH), 1650 (C=O), 1390 (—$SO_2N$—) cm$^{-1}$; $\delta_H$ (DMSO-$d_6$) 6.76 (1H, s, C-3-$\underline{H}$), 7.2 (1H, s, C-6-$\underline{H}$ or C-8-$\underline{H}$), 7.23 (1H, s, C-8-$\underline{H}$ or C-6-$\underline{H}$), 7.5 (2H, d, J=8.4 Hz, C-3'-$\underline{H}$ and C-5'-H), 8.27 (2H, d, J=9.1 Hz, C-2'-$\underline{H}$ and C-6'-$\underline{H}$), 8.38 (4H, br s, exchanged with $D_2O$, C-4'-$OSO_2N\underline{H}_2$ and C-7-$OSO_2N\underline{H}_2$) and 12.87 (1H, s, C-5-$O\underline{H}$). MS: m/z (+ve ion FAB in m-NBA, rel. intensity) 428.7 [80, (M+H)$^+$], 349.8 [25, (M–$SO_2NH_2$)$^+$], 270.9 [25, (M–$SO_2NH_2$)$^+$]. MS: m/z (–ve ion FAB in m-NBA, rel. intensity) 426.7 [80, (M–H)$^-$], 347.8 [80, (M–H–$SO_2NH_2$)$^-$], 268.9 [50, (M–H–$SO_2NH_2$)$^-$]. Found C, 40.6; H, 2.78; N, 6.31; $C_{15}H_{12}N_2O_9S_2$ requires C, 42.06; H, 2.82; N, 6.54%.

5-Hydroxy flavone-3,7-O,O-bisulphamate (10)

3,5,7-Trihydroxy flavone (75 mg, 0.277 mmol) gave a crude product (0.123 g) which was fractionated on silica (50 g) with chloroform/acetone (4:1), and upon evaporation the third fraction gave a yellow residue (58 mg, 47%) which was recrystallized in ethylacetate/hexane (1:2) to give 10 as yellow crystals (31 mg); m.p. 171–173° C.; $R_f$s=0.26 and 0.54 for chloroform/acetone 4:1 and 2:1 respectively; vmax (KBr) 3360 (—$NH_2$), 3260 (H-bonded —OH), 1660 (C=O), 1390 (—$SO_2N$—) cm$^{-1}$; $\delta_H$ (acetone-$d_6$) 6.81 (1H, d, J=2.2 Hz, C-6-$\underline{H}$), 7.21 (1H, d, J=2.2 Hz, C-8-$\underline{H}$), 7.31 (2H, br s, exchanged with $D_2O$, —$OSO_2N\underline{H}_2$), 7.54 (2H, br s, exchanged with $D_2O$, —$OSO_2N\underline{H}_2$), 7.64 (3H, m, C-3'-$\underline{H}$, C-4'-$\underline{H}$ and C-5'-$\underline{H}$), 8.14 (2H, m, C-2'-$\underline{H}$ and C-6'-$\underline{H}$) and 12.29 (1H, s, C-5-$O\underline{H}$). MS: m/z (+ve ion FAB in m-NBA, rel. intensity) 428.9 [100, (M+H)$^+$], 348.9 [50, (M–$SO_2NH_2$)$^+$], 270.0 [25, (M–$SO_2NH_2$)$^+$]. MS: m/z (–ve ion FAB in m-NBA, rel. intensity) 426.9 [85, (M–H)$^-$], 347.9 [100, (M–H–$SO_2NH_2$)$^-$], 269.0 [80, (M–$SO_2NH_2$)$^-$]. Acc. MS: m/z 429.0086 $C_{15}H_{13}N_2O_9S_2$ requires 429.0063. Found C, 42.11; H, 3.06; N, 6.13; $C_{15}H_{12}N_2O_9S_2$ requires C, 42.06; H, 2.82; N, 6.54%.

5-Hydroxy-4'-methoxy flavone-3,7-O,O-bisulphamate (11)

3,5,7-Trihydroxy-4'-trimethoxy flavone (0.075 g, 0.250 mmol) gave a crude product (0.116 g) which was fractionated on silica (50 g) with chloroform/acetone (4:1), and upon evaporation the third fraction gave a yellow residue (0.054 g, 47%) which was recrystallized in acetone/hexane (1:2) to give 11 as yellow crystals (29 mg); m.p.>192° C. (dec.); $R_f$s=0.19 and 0.55 for chloroform/acetone 4:1 and 2:1 respectively; vmax (KBr) 3420 (—$NH_2$), 1620 (C=O), 1360 (—$SO_2N$—) cm$^{-1}$; $\delta_H$ [acetone-$d_6$] 3.94 (3H, s, C-4'-$OC\underline{H}_3$), 6.80 (1H, s, C-6-$\underline{H}$,), 7.12 (1H, s, C-8-$\underline{H}$), 7.16 (2H, d, J=8.8 Hz, C-3'-$\underline{H}$ and C-5'-$\underline{H}$), 7.39 (2H, br s, exchanged with $D_2O$, —$OSO_2N\underline{H}_2$), 7.50 (2H, s, exchanged with $D_2O$, —$OSO_2N\underline{H}_2$), 8.2 (2H, d, J=6.7 Hz, C-2'-$\underline{H}$ and C-6'-$\underline{H}$) and 12.43 (1H, br s, C-5-$O\underline{H}$). MS: m/z (+ve ion FAB in m-NBA, rel. intensity) 459.1 [100, (M+H)$^+$], 379.1 [55, (M–$SO_2NH_2$)$^+$], 300.1 [15, (M–$SO_2NH_2$)$^-$]. MS: m/z (–ve ion FAB in m-NBA, rel. intensity) 456.2 [20, (M–H)$^-$], 378.1 [100, (M–H–$SO_2NH_2$)$^-$], 299.1 [70, (M–H–$SO_2NH_2$)$^-$]. Acc. MS: m/z 459.0174 $C_{16}H_{15}N_2O_{10}S_2$ requires 459.0168. Found C, 41.98; H, 3.06; N, 6.11; $C_{16}H_{14}N_2O_{10}S_2$ requires C, 41.92; H, 3.08; N, 6.11%.

5-Hydroxy-3',4',5'-Trimethoxy flavone-3,7-O,O-bisulphamate (12) and 5,7-Dihydroxy-3',4',5'-Trimethoxy flavone-3-O-sulphamate (13)

3,5,7-Trihydroxy-3',4',5'-trimethoxy flavone (0.2 g, 0.555 mmol) gave a crude product (0.231 g) which was fractionated on silica (100 g) with chloroform/acetone (4:1), and upon evaporation the third fraction gave a yellow residue (0.108 g, 51%) which was recrystallized in acetone/hexane (1:2) to give 12 as yellow crystals (69 mg); m.p. 124–126° C.; $R_f$s=0.19 and 0.53 for chloroform/acetone 4:1 and 2:1 respectively; vmax (KBr) 3360 (—$NH_2$), 3260 (H-bonded —OH), 1660 (C=O), 1430 (—$SO_2N$—) cm$^{-1}$; $\delta_H$ [DMSO-$d_6$/CDCl$_3$, (1:3)] 3.91 (3H, s, C-4'-$OC\underline{H}_3$), 3.95 (6H, s, C-3'-$OC\underline{H}_3$ and C-5'-$OC\underline{H}_3$), 6.83 (1H, d, J=1.8 Hz, C-6-$\underline{H}$,), 7.12 (1H, d, J=2.2 Hz, C-8-$\underline{H}$), 7.39 (2H, s, C-2'-$\underline{H}$ and C-6'-$\underline{H}$), 7.72 (2H, s, exchanged with $D_2O$, —$OSO_2N\underline{H}_2$), 8.06 (2H, s, exchanged with $D_2O$, —$OSO_2N\underline{H}_2$) and 12.2 (1H, s, C-5-$O\underline{H}$). MS: m/z (+ve ion FAB in m-NBA, rel. intensity) 519.1 [100, (M+H)$^+$], 439.1 [60, (M–$SO_2NH_2$)$^+$], 360.1 [10, (M–$SO_2NH_2$)$^-$]. MS: m/z (–ve ion FAB in m-NBA, rel. intensity) 517.1 [85, (M–H)$^-$], 438.1 [100, (M–H–$SO_2NH_2$)$^-$], 359.1 [80, (M–H–$SO_2NH_2$)$^-$]. Acc. MS: m/z 519.0387 $C_{18}H_{19}N_2O_{12}S_2$ requires 519.0379. Found C, 42.3; H, 3.71; N, 5.11; $C_{18}H_{18}N_2O_{12}S_2$ requires C, 41.7; H, 3.5; N, 5.4%.

The second fraction was collected and upon evaporation gave a yellow residue (53 mg, 30%) which was recrystallized in ethylacetate/hexane (1:2) to give 13 as yellow crystals (26 mg); m.p. 189–192° C., $R_f$s=0.10, 0.32 and 0.62 for chloroform/acetone 8:1, 4:1 and 2:1 respectively; vmax (KBr) 3500 (—$NH_2$), 1660 (C=O), 1390 (—$SO_2N$—) cm$^{-1}$; $\delta_H$ [DMSO-$d_6$/CDCl$_3$, (1:1)] 3.84 (3H, s, C-4'-$OC\underline{H}_3$), 3.91 (6H, s, C-3'-$OC\underline{H}_3$ and C-5'-$OC\underline{H}_3$), 6.27 (1H, s, C-6-$\underline{H}$), 6.51 (1H, s, C-8-$\underline{H}$), 7.33 (2H, s, C-2'-$\underline{H}$ and C-6'-$\underline{H}$), 7.84 (2H, br s, exchanged with $D_2O$, —$OSO_2N\underline{H}_2$), 10.8 (1H, s, C-7-$O\underline{H}$) and 12.43 (1H, s, C-5-$O\underline{H}$). MS: m/z (+ve ion FAB in m-NBA, rel. intensity) 440.1 [100, (M+H)$^+$], 360.1 [80, (M–$SO_2NH_2$)$^+$]. MS: m/z (–ve ion FAB in m-NBA, rel. intensity) 438.1 [100, (M–H)$^-$], 359.1 [80, (M–H–$SO_2NH_2$)$^-$]. Acc. MS: m/z 440.0633 $C_{18}H_{18}NO_{10}S$ requires 440.0651. Found C, 48.3; H, 3.89; N, 3.11; $C_{18}H_{17}NO_{10}S$ requires C, 49.2; H, 3.9; N, 3.19%.

3',4',5'-Trimethoxy flavone-3,7-O,O-bisulphamate (14) and 7-Hydroxy 3',4',5'-Trimethoxy flavone-3-O-sulphamate (15)

3,7-Dihydroxy-3',4',5'-trimethoxy flavone (0.2 g, 0.581 mmol) gave a crude product (0.285 g) which was fractionated on silica (200 g) with chloroform/acetone (4:1), and upon evaporation the third fraction gave a yellow residue (0.212 g, 74%) which was recrystallized in acetone/hexane (1:2) to give 14 as light yellow crystals (123 mg); m.p. 182–184° C.; $R_f$s=0.14 and 0.21 for chloroform/acetone 4:1 and 2:1 respectively; vmax (KBr) 3480 (—$NH_2$), 1610 (C=O), 1420 (—$SO_2N$—) cm$^{-1}$; $\delta_H$ (acetone-$d_6$) 3.85 (3H, s, C-4'-$OC\underline{H}_3$), 3.94 (6H, s, C-3'-$OC\underline{H}_3$ and C-5'-$OC\underline{H}_3$), 7.48 (3H, m, C-6-$\underline{H}$, C-2'-$\underline{H}$ and C-6'-$\underline{H}$), 7.69 (4H, br s, exchanged with $D_2O$, C-3-$OSO_2N\underline{H}_2$ and C-7-$OSO_2N\underline{H}_2$), 7.79 (1H, s, C-8-$\underline{H}$) and 8.27 (1H, d, J=8.3 Hz, C-5-$\underline{H}$). MS: m/z (+ve ion FAB in m-NBA, rel. intensity) 502.9 [100, (M+H)$^+$], 423.0 [60, (M–$SO_2NH_2$)$^+$], 344.1 [10, (M–$SO_2NH_2$)$^+$]. MS: m/z (–ve ion FAB in m-NBA, rel. intensity) 501.0 [100, (M–H)$^-$], 422.0 [80, (M–H–$SO_2NH_2$)$^-$], 343.0 [75, (M–$SO_2NH_2$)$^-$]. Acc. MS: m/z 503.0444 $C_{18}H_{19}N_2O_{11}S_2$ requires 503.0430. Found C, 42.2; H, 3.61; N, 5.38; $C_{18}H_{18}N_2O_{11}S_2$ requires C, 43.03; H, 3.61; N, 5.58%.

The second fraction was collected and upon evaporation gave a light yellow residue (12 mg) to give 15; m.p 159–162° C.; $R_f$s=0.23 and 0.50 for chloroform/acetone 4:1 and 2:1 respectively; vmax (KBr) 3500 (—NH$_2$), 3250 (H-bonded —OH), 1620 (C=O), 1420 (—SO$_2$N—) cm$^{-1}$. MS: m/z (+ve ion FAB in m-NBA, rel. intensity) 424.0 [100, (M+H)$^+$], 344.0 [70, (M+H–SO$_2$NH$_2$)$^+$]. MS: m/z (–ve ion FAB in m-NBA, rel. intensity) 422.0 [100, (M–H)$^-$], 343.0 [70, (M–H–SO$_2$NH$_2$)$^-$]. Acc. MS: m/z (FAB)$^+$ 424.0702 C$_{18}$H$_{18}$NO$_9$S requires 424.0703.

5-Hydroxy-4'-methoxyisoflavone 7-O-sulphamate (16)

5,7-Dihydroxy-4'-methoxyisoflavone (0.8 g, 2.817 mmol) gave crude product (0.65 g) which was fractionated on silica (200 g) with chloroform/acetone (8:1). Upon evaporation, the second fraction gave a yellow residue (0.266 g, 26%) which was recrystallised in ethyl acetate/hexane (1:1) to give 16 as yellow crystals (0.211 g), m.p. 184–188° C.; $R_f$s=0.22 and 0.59 for chloroform/acetone 8:1 and 4:1 respectively; vmax (KBr) 3300 (—NH$_2$), 1660 (C=O), 1400 (—SO$_2$N—) cm$^{-1}$; $\delta_H$ (acetone-d$_6$) 3.86 (3H, s, -C-4'-OC$\underline{H}_3$), 6.75 (1H, d, J=2.2 Hz, C-6-$\underline{H}$ or C-8-$\underline{H}$), 7.04 (3H, m, C-6-$\underline{H}$ or C-8-$\underline{H}$, and C-3'-$\underline{H}$ and C-5'-$\underline{H}$), 7.49 (2H, br s, exchanged with D$_2$O, —OSO$_2$N$\underline{H}_2$), 7.58 (2H, d, J=7.0 Hx, C-2'-$\underline{H}$ and C-6'-$\underline{H}$), 8.41 (1H, s, C-2-$\underline{H}$), 13.05 (1H, br s, exchanged with D$_2$O, C-5-O$\underline{H}$). MS: m/z (+ve ion FAB in m-NBA, rel. intensity) 364.0 [100, (M+H)$^+$], 284.1 [12, (M–SO$_2$NH$_2$)$^+$]. MS: m/z (–ve ion FAB in m-NBA, rel. intensity) 515.1 [12, (M–H+m-NBA)$^-$], 362.1 [100, (M–H)$^-$], 283.1 [70, (M–H–SO$_2$NH$_2$)$^-$]. Acc. MS (+ve ion FAB in m-NBA): m/z 364.0494, C$_{16}$H$_{14}$NO$_7$S requires 364.0491. Found: C, 52.8; H, 3.65; N, 3.81. C$_{16}$H$_{13}$NO$_7$S requires C, 52.89; H, 3.61; N, 3.85%.

5-Hydroxy isoflavone-4',7-O,O-bisulphamate (17) and 5,7-Dihydroxy isoflavone-4'-O-sulphamate (16)

4',5,7-Trihydroxy isoflavone (0.5 g, 1.85 mmol) gave a crude product (0.65 g) which was fractionated on silica (200 g) with chloroform/acetone (4:1), and upon evaporation the third fraction gave light yellow residue (0.329 g, 51%) which was recrystallized in ethylacetate/hexane (1:2) to give 17 as beige crystals (0.197 g); m.p.=>198° C. (dec.); $R_f$s=0.14 and 0.24 for chloroform/acetone 4:1 and 2:1 respectively; vmax (KBr) 3460 (—NH$_2$), 1650 (C=O), 1400 (—SO$_2$N—) cm$^{-1}$; $\delta_H$ (acetone-d$_6$) 6.78 (1H, d, J=2.2 Hz, C-6-$\underline{H}$ or C-8-$\underline{H}$), 7.03 (1H, d, J=2.2 Hz, C-8-$\underline{H}$ or C-6-$\underline{H}$) 7.4 (4H, br s, exchanged with D$_2$O, C-4'-OSO$_2$N$\underline{H}_2$ and C-7-OSO$_2$N$\underline{H}_2$), 7.43 (2H, d, J=8.4 Hz, C-3'-$\underline{H}$ and C-5'-$\underline{H}$ or C-2'-$\underline{H}$ and C-6'-$\underline{H}$),, 7.72 (2H, d, J=8.4 Hz, C-2'-H and C-6'-H or C-3'-H and C-5'-H), 8.51 (1H, s, C-2-H) and 12.93 (1H, s, C-5-O$\underline{H}$). MS: m/z (+ve ion FAB in m-NBA, rel. intensity) 428.9 [100, (M+H)$^+$], 350.0 [20, (M+H–SO$_2$NH$_2$)$^+$], 272.1 [30, (M–H–SO$_2$NH$_2$)$^{30}$]. MS: m/z (–ve ion FAB in m-NBA, rel. intensity) 426.9 [100, (M–H)$^-$], 347.9 [95, (M–H–SO$_2$NH$_2$)$^-$], 269.0 [30, (M–H–SO$_2$NH$_2$)$^-$]. Acc. MS: m/z (FAB)$^+$ 429.0083 C$_{15}$H$_{13}$N$_2$O$_9$S$_2$ requires 429.0063. Found C, 42.0; H, 2.91; N, 6.45; C$_{15}$H$_{12}$N$_2$O$_9$S$_2$ requires C, 42.06; H, 2.82; N, 6.54%.

The second fraction was collected and upon evaporation gave light yellow residue (0.112 g, 17%) which was recrystallized in ethylacetate/hexane (1:3) to give 18 as a pale white crystals (0.068 g); m.p.=189–192° C.; $R_f$s=0.23 and 0.33 for chloroform/acetone 4:1 and 2:1 respectively; vmax (KBr) 3500–3300 (—NH$_2$), 3200 (H-bonded —OH), 1680 (C=O), 1610, 1400 (—SO$_2$N—) cm$^{-1}$; $\delta_H$ (acetone-d$_6$) 6.32 (1H, d, J=2.2 Hz, C-6-$\underline{H}$ or C-8-$\underline{H}$), 6.46 (1H, d, J=2.2 Hz, C-8-$\underline{H}$ or C-6-$\underline{H}$), 7.32 (2H, br s, exchanged with D$_2$O, —SO$_2$N$\underline{H}_2$), 7.42 (2H, t, J=8.4 Hz, C-3'-$\underline{H}$ and C-5'-$\underline{H}$ or C-2'-$\underline{H}$ and C-6'-$\underline{H}$), 7.69 (2H, d, J=8.4 Hz, C-2'-$\underline{H}$ and C-6'-H or C-3'-$\underline{H}$ and C-5'-$\underline{H}$) 8.31 (1H, s, C-2-$\underline{H}$), 9.53 (1H, s, C-7-O$\underline{H}$) and 12.9 (1H, s, C-5-O$\underline{H}$). MS: m/z (+ve ion FAB in m-NBA, rel. intensity) 350.0 [100, (M+H)$^+$], 271.1 [15, (M+H–SO$_2$NH$_2$)$^+$]. MS: m/z (–ve ion FAB in m-NBA, rel. intensity) 347.9 [100, (M–H)$^-$], 269.0 [20, (M–H–SO$_2$NH$_2$)$^-$]. Acc. MS: m/z (FAB)$^+$ 350.0347 C$_{15}$H$_{12}$NO$_7$S requires 350.0335. Found C, 51.0; H, 3.16; N, 3.90; C$_{15}$H$_{11}$NO$_7$S requires C, 51.58; H, 3.17; N, 4.01%.

Isoflavone-4',7-O,O-bisulphamate (19)

4',7-Dihydroxy isoflavone (0.45 g, 1.77 mmol) gave a crude product (0.769 g) which was fractionated on silica (200 g) with chloroform/acetone (4:1), and upon evaporation the second fraction gave a pale white residue (0.553 g, 72%) which was recrystallized in acetone/hexane (1:2) to give 19 as white crystals (0.327 g); m.p.>195° C. (dec.), $R_f$s=0.21 and 0.40 for chloroform/acetone 4:1 and 2:1 respectively; vmax (KBr) 3400 (—NH$_2$), 1640 (C=O), 1360 (—SO$_2$N—) cm$^{-1}$; $\delta_H$ (DMSO-d$_6$) 7.37 (2H, d, J=8.8 Hz, C-3'-$\underline{H}$ and C-5'-$\underline{H}$ or C-2'-$\underline{H}$, and C-6'-$\underline{H}$), 7.42 (1H, dd, $J_{C\text{-}6\text{-}H, C\text{-}8\text{-}H}$=2.2 Hz, J=$_{C\text{-}6\text{-}H, C\text{-}5\text{-}H}$8.8 Hz, C-6-$\underline{H}$), 7.7 (2H, d, J=8.8 Hz, C-2'-$\underline{H}$ and C-6'-$\underline{H}$ or C-3'-$\underline{H}$, and C-5'-$\underline{H}$), 8.09 (2H, br s, exchanged with D$_2$O, —OSO$_2$N$\underline{H}_2$), 8.24 (1H, d, J=8.8 Hz, C-5-$\underline{H}$), 8.36 (2H, br s, exchanged with D$_2$, —OSO$_2$N$\underline{H}_2$), 8.63 (1H, s, C-2-$\underline{H}$). MS: m/z (+ve ion FAB in m-NBA, rel. intensity) 412.9 [100, (M+H)$^+$], 334.0 [25, (M+H–SO$_2$NH$_2$)$^+$], 255.1 [20, (M+H–SO$_2$NH$_2$)$^+$]. MS: m/z (–ve ion FAB in m-NBA, rel. intensity) 410.9 [100, (M–H)$^-$], 332.0 [70, (M–H–SO$_2$NH$_2$)$^-$], 253.0 [30, (M–H–SO$_2$NH$_2$)$^-$]. Acc. MS: m/z (FAB)$^+$ 413.0119 C$_{15}$H$_{13}$N$_2$O$_8$S$_2$ requires 413.0113. Found C, 44.0; H, 2.94; N, 6.62; C$_{15}$H$_{12}$N$_2$O$_8$S$_2$ requires C, 43.69; H, 2.93; N, 6.79%.

5,7-Dihydroxyflavanone 4'-O-sulphamate (20)

4',5,7-Trihydroxyflavanone (1.0 g, 3.675 mmol) gave crude product (0.965 g) which was fractionated on silica (200 g) with chloroform/acetone (2:1) and then (4:1) and upon evaporation, the second fraction gave a pale yellow oil (0.345 g, 34%) which solidified on standing. Subsequent recrystallisation of this solid in ethylacetate/hexane (1:1) gave 20 as white crystals (0.259 g), m.p. 211–213° C.; $R_f$s=0.21 (chloroform/acetone, 4:1); vmax (KBr) 3420 (—NH$_2$), 3260 (H-bonded —OH), 1640 (C=O), 1380 (—SO$_2$N—) cm$^{-1}$; $\delta_H$ (acetone-d$_6$) 2.84 (1H, dd, $J_{AB}$=17.4 Hz and $J_{ax,eq}$=3.1 Hz, C-3-$\underline{H}_B$), 3.19 (1H, dd, $J_{BA}$=16.9 Hz and $J_{ax,ax}$=12.8 Hz, C-3-$\underline{H}_A$), 5.62 (1H, dd, $J_{ax,eq}$=3.1 Hz and $J_{ax,ax}$=12.8 Hz, C-2-$\underline{H}$), 5.98 (1H, d, J=2.0 Hz, C-6-$\underline{H}$ or C-8-$\underline{H}$), 6.01 (1H, d, J=2.0 Hz, C-6-$\underline{H}$ or C-8-$\underline{H}$), 7.20 (2H, br s, exchanged with D$_2$O, —OSO$_2$N$\underline{H}_2$), 7.40 (2H, d, J=8.7 Hz, C-2'-$\underline{H}$ and C-6'-$\underline{H}$ or C-3'-$\underline{H}$ and C-5'-$\underline{H}$), 7.66 (2H, d, J=8.7 Hz, C-3'-$\underline{H}$ and C-5'-$\underline{H}$ or C-2'-$\underline{H}$ and C-6'-$\underline{H}$), 9.65 (1H, br s, C-7-O$\underline{H}$) and 12.15 (1H, s, C-5-O$\underline{H}$). MS: m/z (+ve ion FAB in m-NBA, rel. intensity) 352.0 [100, (M+H)$^+$], 272.1 [14, (M–SO$_2$NH$_2$)$^+$]. MS: m/z (–ve ion FAB in m-NBA, rel. intensity) 504.1 [20, (M+NBA)$^-$], 350.1 [100, (M–H)$^-$], 271.1 [45, (M–H–SO$_2$NH$_2$)$^-$]. Acc. MS (+ve ion FAB in m-NBA): m/z 352.0496 C$_{15}$H$_{14}$NO$_7$S requires 352.0491. Found: C, 51.1; H, 3.68; N, 3.98. C$_{15}$H$_{13}$NO$_7$S requires C, 51.28; H, 3.73; N, 3.99%.

5-Hydroxy 4'-methoxy flavanone-3',7-O,O-bisulphamate (21)

4'-Methoxy-3',5,7-trimethoxy flavanone (1.0 g, 2.637 mmol) gave a crude product (1.672 g) which was fractionated on silica (200 g) with chloroform/acetone (2:1), and upon evaporation the second fraction gave a yellow residue (0.715 g, 43%) which was recrystallized in ethylacetate/ hexane (1:2) to give 20 as yellow crystals (0.513 g); m.p. 186–188° C.; $R_f$s=0.13 and 0.35 for chloroform/acetone 4:1 and 2:1 respectively; vmax (KBr) 3380 (—$NH_2$), 3280 (H-bonded —OH), 1640 (C=O), 1390 (—$SO_2N$—) cm$^{-1}$; $\delta_H$ (acetone-$d_6$) 2.92 (1H, m, C-3-H̲), 3.36 (1H, m, C-3-H̲), 3.91 (3H, s, C-4'-OCH̲$_3$), 5.68 (1H, dd, J=12.8 Hz, C-2-H̲), 6.46 (1H, s, C-6-H̲ or C-8-H̲), 6.49 (1H, s, C-8-H̲ or C-6-H̲), 7.07 (2H, br s, exchanged with $D_2O$, —$OSO_2NH_2$), 7.24 (1H, d, J=8.4 Hz, C-5'-H̲), 7.50 (2H, br s, exchanged with $D_2O$, —$OSO_2NH_2$), 7.55 (1H, dd, $J_{C-6'-H, C-5'-H}$=8.4 Hz, $J_{C-6'-H, C-2'-H}$=2.2 Hz, C-6'-H̲), 7.75 (1H, d, J=2.2 Hz, C-2'-H̲) and 12.02 (1H, s, C-5-OH̲). MS: m/z (+ve ion FAB in m-NBA, rel. intensity) 460.9 [100, (M+H)$^+$], 381.9 [20, (M+H–$SO_2NH_2$)$^+$], 303.0 [25, (M+H–$SO_2NH_2$)$^+$]. MS: m/z (–ve ion FAB in m-NBA, rel. intensity) 458.9 [100, (M–H)$^-$], 379.9 [20, (M–H–$SO_2NH_2$)$^-$], 301.0 [20, (M–H–$SO_2NH_2$)]. Acc. MS: m/z (FAB)$^+$ 461.0337 $C_{16}H_{17}N_2O_{10}S_2$ requires 416.0325. Found C, 41.0; H, 3.51; N, 5.97; $C_{16}H_{16}N_2O_{10}S_2$ requires C, 41.74; H, 3.50; N, 6.08%.

(±) 7,4'-Dihydroxy isoflavane (Equol) (22a)

A suspention of Palladium-on-charcoal (10%, 2.2 g) in glacial acetic acid (15 ml) was treated with oxygen for three days. The suspention catalyst was added to the solution of 4',7-dihydroxy isoflavone (0.5 g, mmol) in diglume (60 ml). After 30 min. of catalytic hydrogenation at atmospheric pressure, the solution was filtered and washed with diglume and hot acetic acid. The combined filtrate were evaporoted by using water vacuum pump followed by high vacuum pump. The curde was dissolved in ethylacetate and wished with sodium bicarbonate (5%) and with water till neutral, dried (MgSO$_4$) filtered and evaporated to give pale white crude (0.385 g) which was recrystallized in aquoes ethanol to give 22a as white crystals (0.361 g), m.p. 156–158° C. (lit. 158° C.). $R_f$s=IR (KBr) 3380–2720 cm$^{-1}$. $\delta_H$ (acetone-$d_6$) 2.89 (2H, m, C-4-H̲$_2$), 3.1 (1H, m, C-3-H̲), 3.94 (1H, t, J=10.38 Hz, C-2-H̲$_A$), 4.18 (1H, m, C-2-H̲$_E$), 6.29 (1H, d, $J_{C-8-H \& C-6-H}$=2.44 Hz, C-8-H̲), 6.37 (1H, dd, $J_{C-6-H \& C-7-H}$=8.24 Hz, $J_{C-6-H \& C-8-H}$=2.44 Hz, C-6-H̲), 6.82 (2H, dd, $J_C$-3'-H & C-2'-H=8.55 Hz, $J_C$-3' & C-5-H=2.74 Hz, C-3'-H̲ and C-5'-H̲ or C-2'-H̲ and C-6'-H̲), 6.89 (1H, d, $J_{C-5-H \& C-6-H}$=8.24 Hz, C-5-H̲), 7.16 (2H, dd, $J_{C-2'-H \& C-5'-H}$=8.24 Hz, $J_{C-2'-H \& C-6'-H}$=2.74 Hz, C-2'-H̲ and C-6'-H̲ or C-3'-H̲ and C-5'-H̲), 8.15 (1H, br s, C-7-OH̲ or C-4'-OH̲) and 828 (1H, br s, C-4'-OH̲ or C-7-OH̲).

$^{13}$CNMR (acetone-$d_6$)

MS: m/z (+ve ion FAB in m-NBA, rel. intensity) 242.1 [100, (M)$^+$], [, (M–$SO_2NH_2$)$^+$]. MS: m/z (–ve ion FAB in m-NBA, rel. intensity) 394.2 [50, (M–H+NBA)$^-$], 241.2 [100, (M–H)$^-$]. Acc. MS (+ve ion FAB in m-NBA): m/z 242.094 $C_{15}H_{15}O_3$ requires 243.1021. Found: C,; H, 4. $C_{15}H_{14}O_3$ requires C, 74.36; H, 5.82%.

(±) Isoflavane-7,4'-O,O-bisulphamate (22)

(±) Equol (0.15 g, 0.619 mmol) gave crude product (0.254 g) which was fractionated on silica (100 g) with chloroform/acetone (8:1) and then (4:1) upon evaporation, the second fraction gave brown residue (96 mg, 38%) which was recrystallisation in acetone/hexane (1:2) gave 22 as light brown crystals (61 mg), m.p. ° C.; $R_f$s=(chloroform/acetone, 4:1); vmax (KBr) 3160 (—$NH_2$), 1380 (—$SO_2N$—) cm$^{-1}$; $\delta_H$ (acetone-$d_6$) 3.1 (2H, m, C-4-H̲$_2$), 3.13 (1H, m, C-3-H̲), 4.12 (1H, t, J=10.38 Hz, C-2-H̲$_A$), 4.35 (1H, dd, $J_1$=3.05 Hz and $J_2$=10.68 Hz C-2-H̲$_E$), 6.78 (1H, d, $J_{C-8-H \& C-6-H}$=2.44 Hz, C-8-H̲), 6.84 (1H, dd, $J_{C-6-H \& C-7-H}$=8.44 Hz, $J_{C-6-H \& C-8-H}$=2.44 Hz, C-6-H̲), 7.13 (4H, br s, exchanged with $D_2O$, C-7-$OSO_2NH_2$ & C-4'-$OSO_2NH_2$), 7.18 (1H, d, $J_{C-5-H \& C-6-H}$=8.24 Hz, C-5-H̲), 7.32 (2H, m, C-3'-H̲ and C-5'-H̲ or C-2'-H̲ and C-6'-H̲), 7.44 (2H, m, C-2'-H̲ and C-6'-H̲ or C-3'-H̲ and C-5'-H̲), MS: m/z (+ve ion FAB in m-NBA, rel. intensity) [100, (M+H)$^+$], [, (M–$SO_2NH_2$)$^+$]. MS: m/z (–ve ion FAB in m-NBA, rel. intensity) [, (M+NBA)$^-$], [100, (M–H)$^-$], [, (M–H–$SO_2NH_2$)$^-$]. Acc. MS (+ve ion FAB in m-NBA): m/z $C_{15}H_{17}N_2O_7S_2$ requires 401.04772. Found: C, 44.6; H, 4.0; N, 6.54. $C_{15}H_{16}N_2O_7S_2$ requires C, 44.99; H, 4.03; N, 7.0%.

Biology

Sulphatase Inhibition: Sulphatase inhibition was accessed by using intact MCF-7 breast cancer cells as described previously.

Aromatase Inhibition: Placental microsomes were used to access the aromatase inhibitory properties of the flavonoid sulphamates using the tritiated water release assay[11]. Placental microsomes (200 μg protein) were incubated with [1β-$^3$H] androstenedione (60 nM) and NADPH (1 μM) in the absence or presence of inhibitor (10 μM).

The invention claimed is:

1. A sulphamate compound of general formula XII;

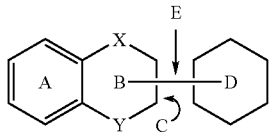

XII wherein A represents the first ring structure, B represents the third ring structure, D represents the second ring structure, E is a bond, X is $CH_2$ or C=O, and Y is $CH_2$ or O; and wherein ring structure has bound thereto a sulphamate group.

2. A compound according to claim 1 wherein if the sulphamate group on the compound were replaced with a sulphate group to form a sulphate compound, then that sulphate compound would be hydrolysable by an enzyme having steroid sulphatase (E.C.3.1.6.2) activity.

3. A compound according to claim 1 wherein the first ring structure and the second ring structure are substituted.

4. A compound according to claim 1 wherein the third ring structure is a heterogeneous ring structure.

5. A compound according to claim 1 wherein X is C=O.

6. A compound according to claim 1 wherein Y is O.

7. A compound according to claim 1 wherein the compound of the present invention is a sulphamate of any one of a flavone, an isoflavone or a flavanone.

8. A compound according to claim 7 wherein the compound is any one of a compound of the general formula IV, a compound of the general formula V or a compound of the general formula VI;

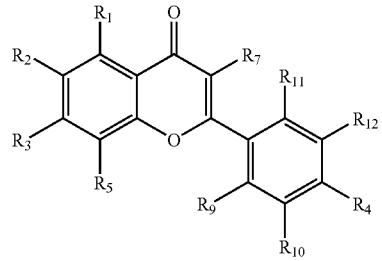

IV

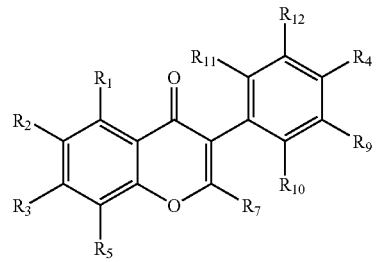

V

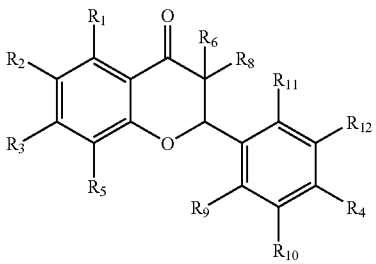

VI

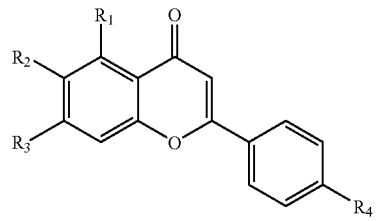

VII

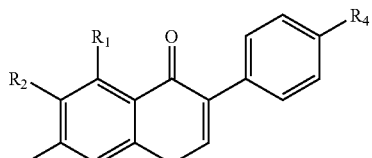

VIII

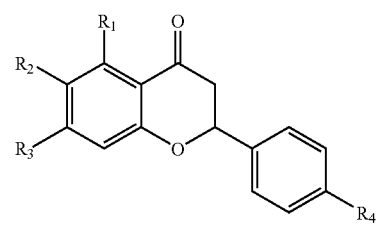

IX wherein $R_1$–$R_{12}$ are independently selected from H, OH, a halogen, an amine, an amide, a suplhonamine, a sulphonamide, any other sulphur containing group, a saturated or unsaturated $C_{1-10}$ alkyl, an aryl group, a saturated or unsaturated $C_{1-10}$ ether, a saturated or unsaturated $C_{1-10}$ ester, and a phosphorous containing group; and wherein at least one of $R_1$–$R_{12}$ is a sulphamate group.

9. A compound according to claim 8 wherein the sulphamate group has the general formula of $OSO_2NR_{13}R_{14}$ wherein $R_{13}$ and $R_{14}$ are independently selected from H, OH, a halogen, a saturated or unsaturated $C_{1-10}$ alkyl, an aryl group, a saturated or unsaturated $C_{1-10}$ ether, a saturated or unsaturated $C_{1-10}$ ester.

10. A compound according to claim 8 wherein $R_1$–$R_{12}$ are independently selected from H, OH, $OSO_2NR_{13}R_{14}$, O—$CH_3$, wherein at least one of $R_1$–$R_{12}$ is $OSO_2NR_{13}R_{14}$, and wherein $R_{13}$ and $R_{14}$ are independently selected from H, OH, a halogen, a saturated or unsaturated $C_{1-10}$ alkyl, an aryl group, a saturated or unsaturated $C_{1-10}$ ether, a saturated or unsaturated $C_{1-10}$ ester.

11. A compound according to claim 8 wherein $R_{13}$ and $R_{14}$ are H.

12. A compound according to claim 9 wherein $R_{13}$ and $R_{14}$ are H.

13. A compound according to claim 10 wherein $R_{13}$ and $R_{14}$ are H.

14. A compound according to claim 1 wherein the compound is a sulphamate of any one of the flavones of formula VII, the isoflavones of formula VIII or the flavanones of formula IX wherein $R_1$–$R_4$ are independently selected from H, OH, a halogen, an amine, an amide, a sulphonamine, a sulphonamide, any other sulphur containing group, a saturated or unsaturated $C_{1-10}$ alkyl, an aryl group, a saturated or unsaturated $C_{1-10}$ ether, a saturated or unsaturated $C_{1-10}$ ester, and a phosphorous containing group; and wherein at least one of $R_1$–$R_4$ is a sulphamate group.

15. A compound according to claim 14 wherein the sulphamate group is on $R_4$.

16. A compound according to claim 1 wherein the compound is a flavanoid sulphamate.

17. A composition for inhibiting oestrone sulphatase activity and aromatase activity comprising a compound according to claim 1.

18. A pharmaceutical composition comprising a compound according to claim 1; and a pharmaceutically acceptable carrier, excipient or diluent.

19. A pharmaceutical composition comprising a compound according to claim 8; and a pharmaceutically acceptable carrier, excipient or diluent.

20. A pharmaceutical composition comprising a compound according to claim 11; and a pharmaceutically acceptable carrier, excipient or diluent.

* * * * *

UNITED STATES PATENT AND TRADEMARK OFFICE
CERTIFICATE OF CORRECTION

PATENT NO. : 7,129,269 B2
APPLICATION NO. : 10/327500
DATED : October 31, 2006
INVENTOR(S) : Reed et al.

It is certified that error appears in the above-identified patent and that said Letters Patent is hereby corrected as shown below:

Column 36, Claim 1, lines 20-35, should read;

A sulphamate compound of general formula XII;

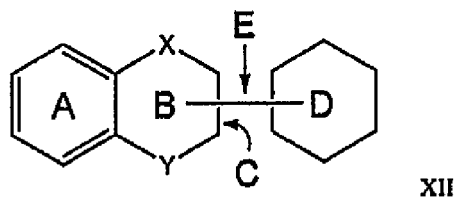

wherein A represents the first ring structure, B represents the third ring structure, D represents the second ring structure, E is a bond, X is $CH_2$ or C=O, and Y is $CH_2$ or and wherein ring structure --A-- has bound thereto a sulphamate group.

Signed and Sealed this

Eleventh Day of December, 2007

JON W. DUDAS
*Director of the United States Patent and Trademark Office*

UNITED STATES PATENT AND TRADEMARK OFFICE
CERTIFICATE OF CORRECTION

PATENT NO.       : 7,129,269 B2
APPLICATION NO.  : 10/327500
DATED            : October 31, 2006
INVENTOR(S)      : Reed et al.

It is certified that error appears in the above-identified patent and that said Letters Patent is hereby corrected as shown below:

Column 36, Claim 1, lines 20-35, should read;

A sulphamate compound of general formula XII;

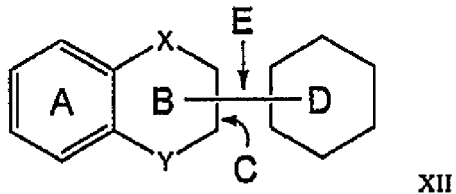

XII wherein A represents the first ring structure, B represents the third ring structure, D represents the second ring structure, E is a bond, X is $CH_2$ or C=O, and Y is $CH_2$ or O; and wherein ring structure --A-- has bound thereto a sulphamate group.

This certificate supersedes the Certificate of Correction issued December 11, 2007.

Signed and Sealed this

Sixteenth Day of September, 2008

JON W. DUDAS
*Director of the United States Patent and Trademark Office*